(12) United States Patent
Hochman

(10) Patent No.: US 6,573,063 B2
(45) Date of Patent: *Jun. 3, 2003

(54) METHODS AND SYSTEMS FOR ASSESSING BIOLOGICAL MATERIALS USING OPTICAL AND SPECTROSCOPIC DETECTION TECHNIQUES

(75) Inventor: Daryl W. Hochman, Bahama, NC (US)

(73) Assignee: Cytoscan Sciences, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/001,366

(22) Filed: Oct. 30, 2001

(65) Prior Publication Data

US 2002/0055092 A1 May 9, 2002

Related U.S. Application Data

(63) Continuation-in-part of application No. 09/629,046, filed on Jul. 31, 2000, now Pat. No. 6,319,682, which is a continuation of application No. 09/326,008, filed on Jun. 4, 1999, now Pat. No. 6,096,510, which is a continuation-in-part of application No. 08/949,416, filed on Oct. 14, 1997, now Pat. No. 5,976,825, which is a continuation of application No. 08/539,296, filed on Oct. 4, 1995, now Pat. No. 5,902,732.
(60) Provisional application No. 60/088,494, filed on Jun. 8, 1998.

(51) Int. Cl.[7] ............................. C12Q 1/02; C12Q 1/00; C12Q 1/24
(52) U.S. Cl. ..................... 435/29; 435/4; 435/30; 435/288.7; 435/32; 435/968
(58) Field of Search .................. 435/29, 4, 30, 435/288.7, 32, 968

(56) References Cited

U.S. PATENT DOCUMENTS 4,284,355 A  *  8/1981  Hansen et al. ............... 356/335
4,736,307 A     4/1988  Salb ............................ 364/518

(List continued on next page.)

FOREIGN PATENT DOCUMENTS

WO      2000037616    * 12/1999    ............... 435/29

OTHER PUBLICATIONS

Hochna, Daryl W. et al., "Dissociation of Synchronization and Excitability in Furosemide Blockade of Epileptiform Activity," Science, vol. 270, pp. 99–103 (Oct. 6, 1995)0.

Haglung, Michael M., M.D. et al., "Enchanced Optical Imaging of Human Gliomas and Tumor Margins," Neurosurgery, vol. 38, No. 2, pp. 308–317 (Feb. 1996).

(List continued on next page.)

Primary Examiner—Louise N. Leary
(74) Attorney, Agent, or Firm—Ann W. Speckman; Janet Sleath

(57) ABSTRACT

Optical detection techniques for the assessment of the physiological state, health and/or viability of biological materials are provided. Biological materials which may be examined using such techniques include cells, tissues, organs and subcellular components. The inventive techniques may be employed in high throughput screening of potential diagnostic and/or therapeutic agents.

19 Claims, 11 Drawing Sheets

(2 of 11 Drawing Sheet(s) Filed in Color)

U.S. PATENT DOCUMENTS

| | | | |
|---|---|---|---|
| 4,768,513 A | 9/1988 | Suzuki | 128/634 |
| 4,972,331 A | 11/1990 | Chance | 364/550 |
| 5,162,204 A * | 11/1992 | Matsuzaki et al. | 435/29 |
| 5,215,095 A | 6/1993 | Macvicar et al. | 128/665 |
| 5,270,173 A * | 12/1993 | Yonemori et al. | 435/29 |
| 5,369,469 A | 11/1994 | Alfano et al. | 356/446 |
| 5,413,108 A | 5/1995 | Alfano | 128/665 |
| 5,438,989 A | 8/1995 | Hochman et al. | 128/653.1 |
| 5,465,718 A | 11/1995 | Hochman et al. | 128/653.1 |
| 5,507,287 A | 4/1996 | Palcic et al. | 128/633 |
| 5,580,748 A * | 12/1996 | Alkon et al. | 435/29 |
| 5,585,401 A * | 12/1996 | Bandt et al. | 514/562 |
| 5,605,811 A * | 2/1997 | Seubert et al. | 435/29 |
| 5,699,798 A | 12/1997 | Hochman et al. | 128/653.1 |
| 5,706,821 A | 1/1998 | Matcher et al. | 128/665 |
| 5,713,352 A | 2/1998 | Essenpreis et al. | 128/633 |
| 5,807,261 A | 9/1998 | Benaron et al. | 600/473 |
| 5,840,035 A | 11/1998 | Heusmann et al. | 600/477 |
| 5,845,639 A | 12/1998 | Hochman et al. | 128/653.1 |
| 5,854,851 A | 12/1998 | Bamberger et al. | 382/132 |
| 5,855,205 A | 1/1999 | Papaionnou | 128/664 |
| 5,865,738 A | 2/1999 | Morcos et al. | 600/365 |
| 5,866,074 A | 2/1999 | Chapman et al. | 422/82.09 |
| 5,902,732 A * | 5/1999 | Hochman | 435/29 |
| 5,976,825 A * | 11/1999 | Hochman | 435/29 |
| 6,096,510 A * | 8/2000 | Hochman | 435/29 |
| 6,319,682 B1 * | 11/2001 | Hochman | 435/29 |

OTHER PUBLICATIONS

Haglund, Michael M., M.D. et al., "Enhanced Optical Imaging of Rat Gliomas and Tumor Margins," *Neurosurgery*, vol. 35, No. 5, pp. 930–941 (Nov. 1994).

Haglund, Michael M., M.D. et al., "Optical imaging of epileptiform and functional activity in human cerebral cortex," *Nature*, vol. 358, No. 20, pp. 668–671 (Aug. 1992).

Hochman, Daryl W., PhC, "Intrinsic Optical Changes in Neuronal Tissue," *Neurosurgery Clinics of North America*, vol. 8, No. 3, pp. 393–412 (Jul. 1997).

Snow, Robert W. et al., "Electrophysiological and Optical Changes in Slices of Rat Hippocampus During Spreading Depression," *Journal of Neurophysiology*, vol. 50, No. 3, pp. 561–572 (Sept. 1983).

Verkman, A.S., "Optical Methods to Measure Membrane Transport Processes," *The Journal of Membrane Biology*, vol. 148, pp. 99–110 (1995).

Echevarria, Miriam et al., "Optical Measurement of Osmotic Water Transport in Cultured Cells," *J. Gen. Physiol.*, vol. 99, pp. 573–589 (Apr. 1992).

Newell, D.W. et al., "Glutamate and Non–Glutamate Receptor Mediated Toxicity Caused by Oxygen and Glucose Deprivation in Organotypic Hippocampal Cultures," *The Journal of Neuroscience*, vol. 15, No. 11, pp. 7702–7711 (Nov. 1995).

Barth, A. et al., "Optical Imaging of Acute Ischemic Injury in Hippocampal Slice Cultures," *Society for Neuroscience*, vol. 22, p. 1424, § 560.9, (1996).

Barth et al., Optical Imaging of Acute Iscemic Injury in Hippocampal Slice Cultures (Abstract), Society for Neurosciencde, vol. 22, p. 1424, 1996.

Hochman, Intrinsic Optical Changes in Neuronal Tissue, Neurosurgery Clinics of North America, vol. 8, No. 3, p. 393, Jul. 1997.

Hochman et al., Dissociation of Synchronization and Excitability in Furosemide Blockade of Epileptiform Activity, Sciente , vol. 270, p. 99, Oct. 6, 1995.

Echevarria et al., Optical Measurement of Osmotic Water Transport in Cultured Cells, J. Gen. Physiol., vol. 99, p. 573, 1992.

Verkman, Optical Methods to Measure Membrane Transport Processes, J. Membrane Biol., vol. 148, p. 99, 1995.

Nicholson et al., Hindered Diffusion of High Molecular Weight Compounds in Brain Extracellular Microenvironment Measured with Integrative Optical Imaging, Biophysical Jounral, vol. 65, p. 2277, 1993.

Guggino et al. CA:103:102292j; J. Gen. Physiol. 86(1): 31–58, 1985.*

* cited by examiner

Fig. 5A2  Fig. 5B2  Fig. 5C2
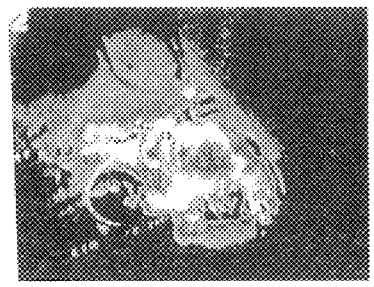
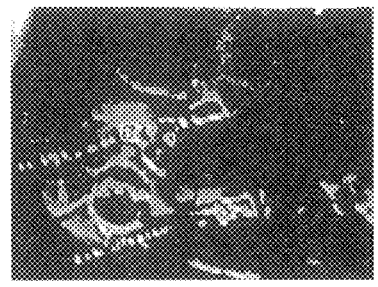
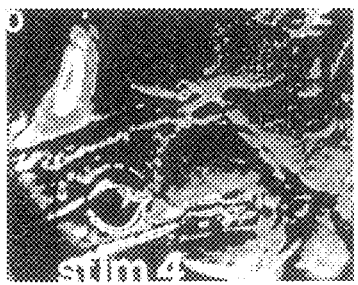
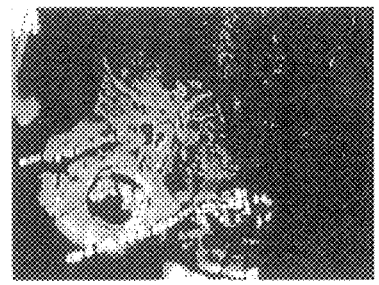
Fig. 5A4  Fig. 5B4  Fig. 5C4

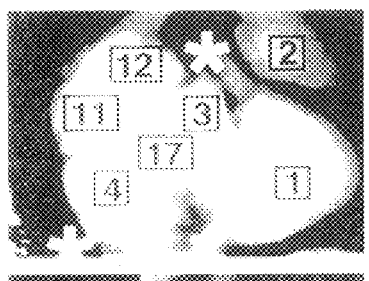
Fig. 8A1
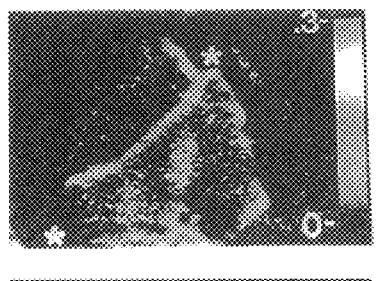
Fig. 8A2
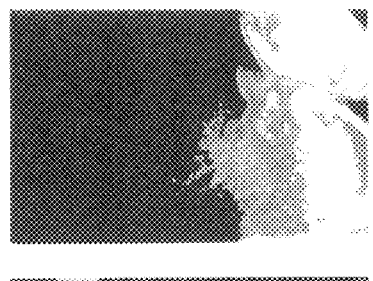
Fig. 8A3
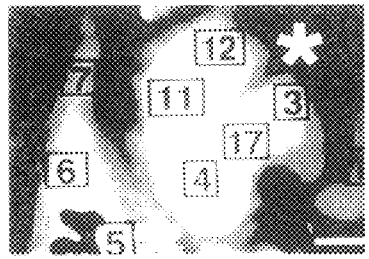
Fig. 8B1
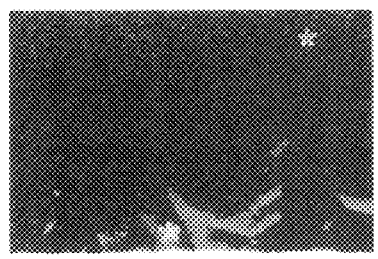
Fig. 8B2
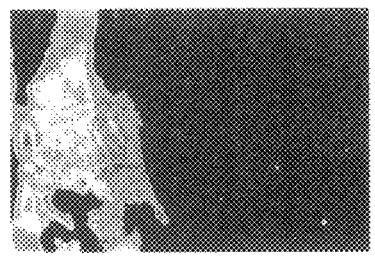
Fig. 8B3

METHODS AND SYSTEMS FOR ASSESSING BIOLOGICAL MATERIALS USING OPTICAL AND SPECTROSCOPIC DETECTION TECHNIQUES

REFERENCE TO RELATES APPLICATIONS

This application is a continuation-in-part application of U.S. patent application Ser. No. 09/629,046, filed Jul. 31, 2000, now U.S. Pat. No. 6,319,682 issued Nov. 20, 2001, which is a continuation of U.S. patent application Ser. No. 09/326,008, filed Jun. 4, 1999, now U.S. Pat. No. 6,096,510 issued Aug. 1, 2000, which is a continuation-in-part of U.S. patent application Ser. No. 08/949,416, filed Oct. 14, 1997, now U.S. Pat. No. 5,976,825, issued Nov. 2, 1999, which is a continuation of U.S. patent application Ser. No. 08/539, 296, filed Oct. 4, 1995, now U.S. Pat. No. 5,902,732, issued May 11, 1999 and claims benefit of Provisional Application No. 60/088,494 filed Jun. 8, 1998.

FIELD OF THE INVENTION

The methods and system of the present invention employ optical, or spectroscopic, detection techniques for assessing the health physiological condition, and viability of biological materials such as tissues, cells, and subcellular components, and may be used in both in vitro and in vivo systems. One important application of the methods and apparatus of the present invention is high throughput screening of candidate agents and conditions to evaluate their suitability as diagnostic or therapeutic agents.

BACKGROUND OF THE INVENTION

Biology has undergone a change so fundamental that it has been compared to the industrial revolution of the $19^{th}$ century and the advances in quantum physics in the $20^{th}$, century. The complete sequencing of the human genome and of the genomes of many microbes and plants has given rise to genomics, the discipline defined as the study of the structure and function of large number of genes undertaken in a simultaneous fashion. While the value of genomics as a basic tool for biological research has been clearly demonstrated, the impact on drug discovery remains unrealized. It is now clear that knowledge of gene sequences does not imply an understanding of their function. For example, inferred function based on the study of homologs from model organisms allows only the assignment of function to approximately 10% of the genes of mouse and humans. Clearly, the understanding of the function of genes at all organizational levels of biology will be the primary challenge of the post-genomics era.

The breadth and scale of the research efforts in genomics and related disciplines has resulted in the generation of large quantities of data that are difficult to examine or understand. Evolving relational databases will include not just primary biological data, but also predictions of protein structure, dynamic models of complex physiological processes, and the statistical treatment of data. The evolution of bioinformatics has occurred in parallel with the creation of increasingly sophisticated tools for compiling and analyzing chemical data. Theoretical and experimental chemical data is being incorporated into advanced chemical databases that are being relationally connected to genomic databases to give rise to the field of chemical genomics. Finally, engineering and the physical sciences play a crucial role in the post-genomics era. Advances in analytical chemistry, analytical biochemistry, image analysis, robotics and process automation have enabled the task of developing advanced biological databases.

In spite of the availability of numerous targets for drug discovery, the overall success rate of the process remains abysmally low. At present, it is fair to say that the question How does one apply information about gene and gene products to the discovery of new drugs remains largely unanswered. There are three main reasons for low success rates in the conversion of vast amounts of genomics information to viable products: (1) lack of clear criteria for target validation; (2) hits to leads decisions based on potency and selectivity against molecular targets, with limited physiological information; and (3) nonviable leads due to poor adsorption, undesirable metabolism, toxicity, or unacceptable side effects.

Drug development programs rely on in vitro screening assays and subsequent testing in appropriate animal models to evaluate drug candidates prior to conducting clinical trials using human subjects. Screening methods currently used are generally difficult to scale up to provide the high throughput screening necessary to test the numerous candidate compounds generated by traditional and computational means. Moreover, studies involving cell culture systems and animal model responses frequently don't accurately predict the responses and side effects observed during human clinical trials.

Conventional methods for assessing the effects of various agents or physiological activities on biological materials, in both in vitro and in vivo systems, generally are not highly sensitive or informative. For example, assessment of the effect of a physiological agent, such as a drug, on a population of cells or tissue grown in culture, conventionally provides information relating to the effect of the agent on the cell or tissue population only at specified points in time. Additionally, current assessment techniques generally provide information relating to a single or a small number of parameters. Candidate agents are systematically tested for cytotoxicity, which may be determined as a function of concentration. A population of cells is treated and, at one or several time points following treatment, cell survival is measured. Cytotoxicity assays generally do not provide any information relating to the cause(s) or time course of cell death.

Similarly, agents are frequently evaluated based on their physiological effects, for example, on a particular metabolic function or metabolite. An agent is administered to a population of cells or a tissue sample, and the metabolic function or metabolite of interest is assayed to assess the effect of the agent. This type of assay provides useful information, but it does not provide information relating to the mechanism of action, the effect on other metabolites or metabolic functions, the time course of the physiological effect, general cell or tissue health, or the like.

Optical techniques have been developed and used for several applications. Light scattering has been used in the past to provide measurements of osmotic water permeability in suspensions of osmotically responsive vesicles and small cells. A. S. Verkman, "Optical Methods to Measure Membrane Transport Processes," *J. Membrane Biol.* 148:99–110, 1995. Another study reported a method for the optical measurement of osmotic water transport in cultured cells. M. Echevarria, A. S. Verkman, "Optical Measurement of Osmotic Water Transport in Cultured Cells: Role of Glucose Transporters," *J. Gen. Physiol.* 99:573–589, 1992.

Optical techniques for observing nerve activity and neuronal tissue are well-established. Hill and Keynes observed that the nerve from the walking leg of the shore crab normally has a whitish opacity caused by light scattering, and that opacity changes evoked by electrical stimulation of that nerve were measurable. Hill, D. K. and Keynes, R. D., "Opacity Changes in Stimulated Nerve," *J. Physiol.* 108:278–281, 1949. Since the publication of those results, experiments designed to learn more about the physiological mechanisms underlying the correlation between optical and electrical properties of neuronal tissue and to develop improved techniques for detecting and recording activity-evoked optical changes have been ongoing.

Intrinsic changes in optical properties of cortical tissue have been assessed by reflection measurements of tissue in response to electrical or metabolic activity. Grinvald, A., et al., "Functional Architecture of Cortex Revealed by Optical Imaging of Intrinsic Signals," *Nature* 324:361–364, 1986; Grinvald, et al., "Optical Imaging of Neuronal Activity, Physiological Reviews, Vol. 68, No. 4, October 1988. Grinvald and his colleagues reported that some slow signals from hippocampal slices could be imaged using a CCD camera without signal averaging.

A CCD camera was used to detect intrinsic signals in a monkey model. Ts'o, D. Y., et al., "Functional Organization of Primate Visual Cortex Revealed by High Resolution Optical Imaging," *Science* 249:417–420, 1990. The technique employed by Ts'o et al. would not be practical for human clinical use, since imaging of intrinsic signals was achieved by implanting a stainless steel optical chamber in the skull of a monkey and contacting the cortical tissue with an optical oil. Furthermore, in order to achieve sufficient signal to noise ratios, Ts'o, et al., had to average images over periods of time greater than 30 minutes per image.

The mechanisms responsible for intrinsic signals are not well understood. Possible sources of intrinsic signals include dilation of small blood vessels, changes in blood flow, volume and oxygenation, neuronal activity-dependent release of potassium, and swelling of neurons and/or glial cells caused, for example, by ion fluxes or osmotic activity. Light having a wavelength in the range of 300 to 3000 nm may also be reflected differently between active and quiescent tissue due to increased blood flow into regions of higher neuronal activity. Yet another factor that may contribute to intrinsic signals is a change in the ratio of oxyhemoglobin and deoxyhemoglobin in blood.

U.S. Pat. No. 5,215,095 discloses methods and apparatus for real time imaging of functional activity in cortical areas of a mammalian brain using intrinsic signals. A cortical area is illuminated, light reflected from the cortical area is detected, and digitized images of detected light are acquired and analyzed by subtractively combining at least two image frames to provide a difference image. U.S. Pat. Nos. 6,196,226 and 6,233,480 disclose similar optical methods and apparatus for optical detection of neuronal tissue and activity.

U.S. Pat Nos. 5,438,989 discloses a method for imaging margins, grade and dimensions of solid tumor tissue by illuminating the area of interest with high intensity electromagnetic radiation containing a wavelength absorbed by a contrast agent, obtaining a background video image of the area of interest, administering a contrast agent, and obtaining subsequent video images that, when compared with the background image, identify the solid tumor tissue as an area of changed absorption. U.S. Pat. Nos. 5,699,798 and 6,241,672 disclose methods and apparatus for optically distinguishing between tumor and non-tumor tissue, and imaging margins and dimensions of tumors during surgical or diagnostic procedures.

U.S. Pat. No. 5,465,718 discloses a method for imaging tumor tissue adjacent to nerve tissue to aid in selective resection of tumor tissue using stimulation of a nerve with an appropriate paradigm activate the nerve, permitting imaging of the active nerve. The '718 patent also discloses methods for imaging of cortical functional areas and dysfunctional areas, methods for visualizing intrinsic signals, and methods for enhancing the sensitivity and contrast of images. U.S. Pat. Nos. 5,845,639 and 6,161,031 disclose optical imaging methods and apparatus for detecting differences in various blood parameters, such as blood flow rates and flow changes, as well as cortical areas of neuronal inhibition.

U.S. Pat. Nos. 5,902,732 and 5,976,825, which are related to this application, disclose methods for screening drug candidate compounds for anti-epileptic activity using glial cells in culture by osmotically shocking glial cells, introducing a drug candidate, and assessing whether the drug candidate is capable of abating changes in glial cell swelling. These patents also disclose a method for screening drug candidate compounds for activity to prevent or treat symptoms of Alzheimer's disease, or to prevent CNS damage resulting from ischemia, by adding a sensitization agent capable of inducing apoptosis and an osmotic stressing agent to CNS cells, adding the drug candidate, and assessing whether the drug candidate is capable of abating cell swelling. U.S. Pat. Nos. 6,096,510 and 6,319,682, which are also related to this application, disclose additional methods and systems for assessing biological materials using optical detection techniques. A method for determining the viability and health of living cells inside polymeric tissue implants is also disclosed, involving measuring dimensions of living cells inside the polymeric matrix, osmotically shocking the cells, and then assessing changes in cell swelling. Assessment of cell swelling activity is achieved by measuring intrinsic optical signals using an optical imaging screening apparatus.

The methods and systems of the present invention are directed to problems that present fundamental limitations in our ability to make the step from the level of genomics and proteonomics to the design of novel therapeutics. The solution to these problems necessarily requires non-destructive methods for extracting quantitative biological responses in living, physiologically meaningful systems and environments. The physiomics approach, described herein, has several requirements that are entirely unique, and set it apart from technologies and methods conventionally applied to molecular biology. This is because the physiological responses in cells and tissues are both spatially and temporally dynamic, and hence require technologies that can monitor changes in living systems that are occurring in distinct spatial locations with high temporal resolution.

SUMMARY OF THE INVENTION

Cells from nearly every organ and tissue, of both plant and animal origin, can be dissociated into single cells, grown and propagated using cell culture techniques. Pathological cells from diseased or dysfunctional tissue can also be isolated and maintained in tissue culture. Various types of tissues, including normal, dysfunctional and malignant tissues, may be maintained under culture conditions for prolonged periods of time and assessed according to methods of the present invention. Short-term experiments may also be conducted on living acute tissue samples that are prepared and maintained under physiological conditions. Many multicellular systems and tissues may also be maintained as functioning systems in cell culture. Healthy, pathogenic and dysfunctional cells and tissue may also be tested and observed in situ in living animal models, including humans, using methods and systems of the present invention.

All cells undergo physiological processes that contribute to and determine their geometrical structure and optical properties. These physiological processes include metabolic processes, volume-regulatory responses, gene expression, endocytosis, pinocytosis, ion homeostasis, immune responses, neurological activity and inhibition, responses to mechanical trauma, chemical and environmental insult, and the like. Various events, including disease states, dysfunction, inflammation, exposure to pathogens, pollutants, radiation, chemotherapy, infectious or other agents, aging, apoptosis, necrosis, oncogenesis, genetic modification, and the like, affect one or more of these physiological processes, producing measurable and predictable changes in the characteristic geometrical structure and/or optical properties of individual cells and/or cell populations.

The methods and systems of the present invention employ optical, or spectroscopic, detection techniques to assess the physiological state of biological materials including cells, tissues, organs, subcellular components and portions of intact organisms. The biological materials may be of human, animal, bacterial, viral or plant origin, or they may be derived from any such materials. Static and dynamic changes in the geometrical structure and/or optical properties of the biological materials in response to the administration of a physiological challenge or a test agent are indicative and predictive of changes in the physiological state or health of the biological material. The physiological responses of cells and tissues to the administration of a physiological challenge or a test agent are both spatially and temporally dynamic, and require monitoring of the changes in living systems with high spatial and temporal resolution. The methods and systems of the present invention provide the technology for monitoring changes in living systems with high spatial and temporal resolution.

Numerous physiological states and conditions may be assessed in cell sample populations, and in situ, in living biological systems, using the optical techniques of the present invention. Cell viability and identification of non-viable and viable cells and tissues may be assessed using the optical techniques described, for example, in U.S. Pat. No. 6,096,510. Tissue hemodynamics, including blood volume and blood oxygenation, may be assessed using the optical techniques described, for example, in U.S. Pat. Nos. 5,845,639 and 6,161,031. Tumor tissue may be identified and characterized using the optical techniques described, for example, in U.S. Pat. Nos. 5,699,798 and 6,241,672. CNS and peripheral nerve activity and inhibition, including neuronal excitability and synchronization, may be assessed using the optical techniques described, for example, in U.S. Pat. Nos. 6,196,226 and 6,233,480. Apoptotic and necrotic cell death processes may be observed and distinguished using the methods and systems described herein. Cell volume regulation and changes are observed as changes in intrinsic optical properties of cell sample populations. Changes in the intrinsic optical properties of cell sample populations, measured as changes in light scattering and absorption, are also indicative and predictive of the physiological state and condition of cell sample populations.

Assessment of intracellular calcium, intracellular pH, intracellular chloride, ATP levels, ATP/ADP ratios, cyclic AMP, oxidative activity, intracellular reactive oxygen species, metabolic state of mitodhondria, cystolic redox potential, nitric oxide, cell motility, mitochondrial transmembrane potential, mitochondrial swelling, lysosome activity, intracellular zinc, intracellular magnesium, intracellular sodium, intracellular potassium, cell membrane potential, cell proliferation and many other cellular, intracellular and biological system conditions, are also observed as changes in intrinsic and/or extrinsic optical properties of cell sample populations. The methods and systems of the present invention thus provide the capability to screen numerous cell populations, tissue types and biological systems and acquire data relating to a wide variety of cellular, intracellular and biological systems conditions.

Another aspect of methods and systems of the present invention involves the development and use of databases cataloging the complex responses of various biological materials including cells, tissues, organs, subcellular components, portions of intact organisms, and the like, to various physiological challenges or test agents. Changes in the geometrical and/or optical properties of living systems induced (or not) by admininstration of a physiological challenge or a test agent are detected with a high degree of spatial and temporal resolution, stored, compared to changes induced in different biological systems and/or by administration of different physiological challenges and/or test agents, and patterns are identified. The changes induced by different physiological challenges and/or test agents on specific biological sample materials have unique profiles that are predictive of various types of responses and are useful for the development and screening of candidate therapeutic and diagnostic compositions.

The database may archive, for example, the spatially and temporally resolved response patterns of cell, tissue and whole animal sample populations to existing, approved therapeutic agents. The spatially and temporally resolved response patterns of candidate agents and combinations may then be compared to and screened against the response patterns of approved and presumably safe and efficacious known agents to predict the response of the candidate agent and/or combination in a biological system. Comparison of screening data against response patterns stored in the database provides valuable assessment of target validation, lead selection and optimization, and detection of side effects.

Two different classes of dynamic phenomena are observed in viable biological materials using optical detection techniques: (1) geometrical changes in the diameter, volume, conformation, intracellular space of individual cells or extracellular space surrounding individual cells; and (2) changes in one or more optical properties of individual cells, intracellular structures or of cell populations. The changes in optical properties may be intrinsic optical changes, such as light scattering, reflection, absorption, refraction, diffraction, birefringence, refractive index, Kerr effect, and the like, that are indicative of various physiological conditions. Alternatively, changes in optical properties may be induced by administration of a test agent such as a dye or another type of contrast agent, such changes in optical properties including changes in absorption, scattering, birefringence, fluorescence, and phosphorescence. Both classes of phenomena may be observed statically or dynamically, with or without the aid of a contrast enhancing agent. Geometrical changes may be assessed directly by measuring (or approximating) the geometrical properties of individual cells, or indirectly by observing changes in the optical properties of cells. Changes in optical properties of individual cells or cell populations may be assessed directly using systems of the present invention.

Observation and interpretation of geometrical and/or optical properties of individual cells and cell populations is achieved in both in vitro and in vivo biologically viable systems without altering characteristics of the sample by applying physiologically invasive materials, such as fixatives, and without using ionizing radiation, microelectrode penetration, or other techniques that are damaging or destructive to the cell population. Physiologically non-invasive contrast enhancing agents, such as vital dyes, markers, probes, and the like, may be used in desired applications to enhance the sensitivity of optical detection techniques. In applications employing contrast enhancing agents, the optical detection techniques are used to assess extrinsic optical properties of the biological materials.

Detection and analysis of the geometrical and/or intrinsic optical properties of individual cells or sample cell populations using techniques that provide a high level of spatial and temporal resolution provides information permitting the classification of the physiological state of individual cells or sample cell populations. Based on analysis of the geometrical and/or optical properties of a sample cell population, the sample may be classified as viable or non-viable, apoptotic, necrotic, proliferating, in a state of activity, inhibition, synchronization, or the like, or in any of a variety of physiological states, all of which produce distinct geometrical and/or optical profiles. The use of probes and labeled markers and assaying of extrinsic optical properties of sample populations to assess various physiological conditions at resolved locations in time and in space provides yet further information relating to cellular and biological systems responses to various physiological challenges and test agents.

An important application of the methods and systems of the present invention involves screening cell populations to assess the effect(s) of exposure to various types of test agents or test conditions, including candidate compounds and combinations, drugs, hormones and other biological agents, toxins, infectious agents, physiological stimuli, radiation, chemotherapy, and the like. Safety and cytotoxicity testing is conducted by exposing a sample population to a test agent or test condition and assessing the physiological state of the sample population using optical techniques at one or more time points following administration of the test agent or test condition. The effect of various test agents and conditions may be evaluated on numerous types of normal and pathological sample populations. Such testing may be conducted on various sample populations to determine how a test agent or condition affects a desired target sample population, as well as to predict whether a test agent or condition produces physiological side effects on sample populations that are not the target of the test agent or condition.

Thus, for example, a candidate for treatment of central nervous system (CNS) conditions may be screened using various types of CNS cell and tissue populations to determine safety and efficacy in the CNS, as well as other types of cell populations, such as renal or hepatic cell populations, to determine safety and efficacy in other portions of the biological system. Similarly, a candidate for treating a cancer may be screened using various types of cancer and normal cell populations to assess the specificity and toxicity of the candidate agent or combination on various cell populations. Additionally, the effect of genetic modifications on the numerous physiological states and conditions described herein may be assessed with respect to various cell and tissue sample populations and compared to unaltered, wild-type sample populations, or to differently genetically altered sample populations.

In addition to assessing the safety and efficacy of a candidate composition or combination, numerous physiological responses of the sample population to the agent, including those described above, may be determined and assessed. Thus, various intracellular responses, such as changes in intracellular properties, such as pH, reactive oxygen species, calcium, chloride, ATP, zinc, magnesium, sodium, potassium, and the like, may be assessed, in addition to changes in other cell-based properties, such as cell membrane potentials and the like, in addition to various cellular and environmental properties, such as changes in intracellular and extracellular volume, light scattering, and the like, in addition to gross changes in the cell sample population, such as changes in viability, apoptotic and necrotic activity. All of these properties and responses may be assessed using the optical methods and systems of the present invention. Analysis of these properties is predictive of the behavior and effect of a candidate composition or combination in a biological system, such as an animal. In yet another aspect, profiles determined for various candidate agents in various types of sample populations may be compared to profiles for various types of sample populations established for other treatment agents having known biological effects. Comparison and analysis of such profiles and patterns within profiles provides accurate prediction of the biological effects of candidate agents within a biological system.

According to one embodiment, a disease state or compromised condition is simulated in biological materials prior to administration of a test agent or test condition to assess the suitability of the test agent or condition for treating the disease state or compromised condition. Exposure of sample populations to a physiological challenge, such as a change in extracellular osmolarity or ion concentration, altered oxygen or nutrient or metabolite conditions, drugs or diagnostic or therapeutic agents, a disturbance in ion homeostasis, electrical stimulation, inflammation, infection with various agents, radiation, and the like, simulates a disease state at a cellular or tissue level. Subsequent exposure of the sample populations a test agent or condition and detection and analysis of changes in geometrical and/or optical properties of the sample populations provides information relating to the physiological state of the sample populations produced by the test agent or condition. Screening techniques may be adapted for use with various types of cell sample populations maintained in vitro under appropriate cell culture conditions to provide a high throughput, automated screening system. Alternatively, screening techniques may be adapted to examine cell and tissue populations using various animal models to assess the effect of a physiological challenge and/or administration of a test agent on various cell populations in animal models in situ. Screening techniques of the present invention may also be implemented to examine cell and tissue populations, using animal and plant models, to assess the effect(s) of genetic modifications of such animal and plant models in situ.

Changes in geometrical and/or optical properties of individual cells or cell sample populations may be compared to empirically determined standards for specific cell types, cell densities and various physiological states, or appropriate controls may be run in tandem with the test samples to provide direct comparative data. Data corresponding to spatial and temporal changes in geometrical and/or optical properties of sample populations is collected and, preferably, stored to provide data relating to the time course and spatial distribution over the time course of the effect of a test agent or condition on sample populations. Strategies for designing screening protocols, including appropriate controls, multiple samples for screening various dosages, activities, and the like, are well known in the art and may be adapted for use with the methods and systems of the present invention.

DESCRIPTION OF THE FIGURES

The patent file contains at least drawing executed in color. Copies of this patent with color drawings will be provided by the Office upon request and payment of the necessary fee.

Preferred embodiments of the methods and systems for assessing biological materials using optical detection techniques of the present invention will be described with reference to the figures, in which:

FIGS. 2A–2C show the effect of the agent furosemide on stimulation-evoked afterdischarge activity in a hippocampal slice comparing the field response measurements at an extracellular electrode, with images highlighting changes in optical properties. Experiments were conducted as described in Example 1.

FIGS. 5A2–5C4 illustrate spatial images of stimulation-induced epileptiform activity. The images show comparisons between different degrees of activation illustrating both the spatial extent and amplitude of optical changes indicative of the extent of cortical activity. Experiments were conducted as described in Example 2.

FIGS. 8A1–8B3 illustrate functional mapping of human language (Broca's area) and tongue and palate sensory area in an awake human patient as described in Example 3. FIGS. 8A1 and 8B2 illustrate control percentage difference images and FIGS. 8A3 and 8B3 illustrate peak optical change images following cortical stimulation.

DESCRIPTION OF PREFERRED EMBODIMENTS

Figure 1:
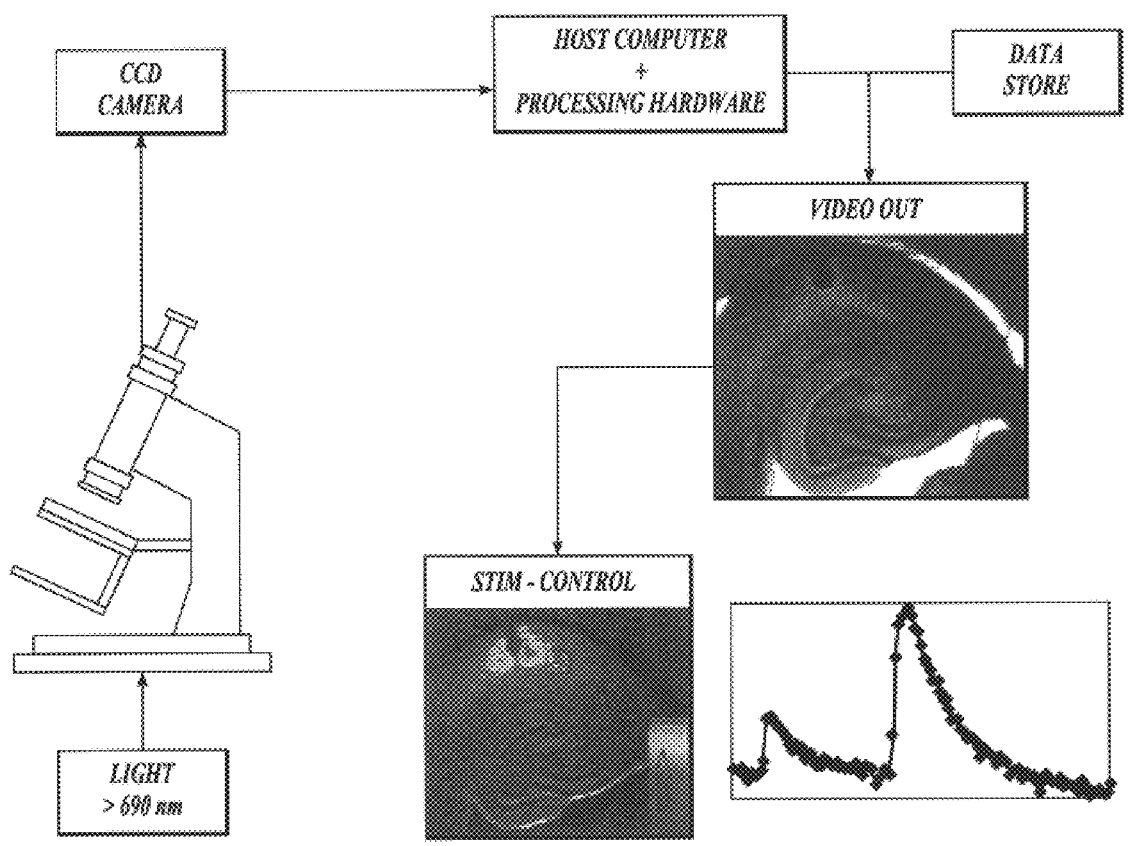
FIG. 1 shows a partially schematic flow diagram illustrating exemplary methods and output of the methods and apparatus of the present invention with reference to in vitro cell populations, wherein intrinsic optical properties of an acute rat hippocampal slice maintained in a submerged perfusion chamber are monitored at intervals during a control period and an activation period, and data is processed according to methods of the present invention.

The following description of preferred embodiments includes detailed descriptions of specific applications, as well as specific methods and apparatus. These specific embodiments are described for purposes of illustrating the scope of the invention; the invention is not limited to these applications. Techniques for acquiring data relating to optical properties of various types of tissues that would be suitable for use with the methods and systems of the present invention are described in numerous U.S. Patents. U.S. Pat. Nos. 5,215,095, 5,438,989, 5,699,798, 5,465,718, 5,845, 639, 5,902,732, 5,976,825, 6,161,031, 6,241,672, 6,196,226, 6,233,480 and 6,096,510 are hereby incorporated herein by reference in their entireties.

One important application of methods and systems of the present invention is to classify the physiological condition or state of biological materials based on their geometrical and/or optical properties, and to distinguish among various physiological conditions. Viable cell populations are distinguishable from non-viable cell populations in both in vitro cell sample populations, and in situ in animal models based on a comparison of geometrical and/or optical properties. Similarly, sample populations that are proliferating, or that are responding to various stimuli by mounting certain responses, such as immune responses, inflammatory responses, and the like, are distinguishable from non-responsive sample populations. In one aspect, methods and systems of the present invention are useful for determining the viability and level of function of cell and tissue implants and engineered cells and tissues. Because methods and systems of the present invention are non-destructive and may be used to assess the physiological condition of cells and tissues in situ in a living biological system, such as an animal, the physiological condition of implanted cells and tissues may be monitored both prior to implantation and, in situ, following implantation.

Cells or cell populations undergoing apoptosis, an active programmed cell death phenomenon, are likewise distinguishable from cells or cell populations undergoing necrosis. Necrosis may result from mechanical injury, exposure to toxins, anoxia due to impairment of the blood supply, or the like. The physiological changes observed during necrosis include swelling, clumping of chromatin, and deterioration of the organelles, followed by lysis with release of the cell contents, which are then phagocytized by macrophages. The cytological changes associated with apoptosis are very different and include an early condensation of chromatin and degradation of DNA, and cell volume decreases, with the cell membrane and the organelles remaining intact. Apoptotic cells ultimately fragment into several membrane-bounded globules that are phagocytized by neighboring cells. Neutrophils and macrophages are not involved in the terminal stages of apoptotic processes to the same extent that they are in necrotic processes.

Identifying cell populations undergoing apoptosis is important for numerous reasons. Certain genes responsible for regulating apoptosis play a role in cancer, and cancer therapy by irradiation, chemotherapy, and hormone treatment all induce apoptosis in tumor cells. Some cancers may, in fact, result from the down-regulation of genes that normally cause apoptosis. Hence, methods for screening cell populations to ascertain whether or not they are apoptotic is central to gaining an insight into various pathological conditions, such as cancer. Since different agents used in cancer treatment induce apoptosis, it is likely that apoptotic pathways are indicative of the outcome of chemotherapy.

There are many other instances of apoptosis during both normal and pathological cellular activities. For example, hormones regulate apoptosis in gonadal tissues so that numbers and development of sperm and egg cells are regulated. In the immune system, apoptosis plays a clear role in the selection of lymphocytes. Immunodeficiency may be caused by lymphocyte developmental blocks which lead to apoptosis by default. Cell death in these cases is the normal, programmed response in the absence of an essential survival signal. However, active induction of programmed cell death can also elicit immunodeficiency, as in acquired immunodeficiency syndrome, AIDS. Considerable evidence supports the proposition that HIV activates T cell apoptosis. In the nervous system, apoptosis plays not only a pivotal role during embryogenesis, but also occurs in the adult, generally under various pathological conditions that are accompanied by devastating consequences for the patients. Examples include Alzheimer's disease, amyotrophoic lateral sclerosis (ALS) and other types of neuronal injury inflicted by ischemia, hypoglycemia or excitotoxic agents. Trauma, stroke, excitoxicity and hypoxia are conditions of ischemia that are associated with extensive neuronal cell death in sensitive brain regions. Recent studies demonstrated that, after experimentally induced ischemia, characteristic apoptotic DNA fragmentation occurs in affected brain regions. Methods and systems of the present invention for classifying cell populations as apoptotic, necrotic, viable, non-viable, and the like, are useful for identifying the physiological state of cells in both in vitro and in vivo systems, as well as for screening various test agents to ascertain whether they are useful as diagnostic or therapeutic agents.

Methods and systems of the present invention may also be used to identify physiological conditions associated with and to evaluate test agents and conditions for diagnosis and treatment of various disorders, and pathological conditions, including migraine headaches, spreading depression, epilepsy, Alzheimer's disease, multiple sclerosis, psychiatric disorders such as depression, anxiety, bipolar disorder, schizophrenia, Parkinson's disease and other neurodegenerative disorders, inflammation, trauma, malignancies such as cancer, angiogenesis, wound healing, immune deficiencies, and the like. Test agents and conditions may also be tested for safety and efficacy for applications such as toxicology, learning and memory, bone growth and maintenance, muscle and blood systems, sensory-input systems, and the like. In addition to safety and efficacy, methods and systems of the present invention provide the capability to screen for and determine specific cellular, intracellular and extracellular responses of sample populations using various dyes, probes, markers and the like.

Optical contrast enhancing agents useful for enhancing the sensitivity of optical detection for various types of cells, physiological states, and the like, may also be screened and identified using methods and systems of the present invention. Sample populations comprising malignant, pathological, or dysfunctional cells may be exposed to test agents, for example, to identify agents that preferentially identify and distinguish malignant, pathological, and dysfunctional cells or tissue. Additionally, dyes, labeled probes, markers and the like, that preferentially segregate at predetermined sites or in response to predetermined physiological conditions, or that are indicative of physiological conditions, such as pH, the presence or concentration of a compound, such as calcium, zinc, potassium, or the like, are also used in methods and systems of the present invention and detected using the optical techniques described herein. Dyes, contrast enhancing agents, probes and markers for determining various physiological conditions and activities, including fluorescent and phosphorescent agents, are known in the art and are available, for example, from Molecular Probes, Inc. of Eugene, Oreg., U.S.A.

According to one embodiment, methods and systems of the present invention acquire and compare data representative of one or more dimensional properties of individual cells or cell samples. Acquisition, processing and analysis of data relating to optical properties is described throughout this description. Acquisition of data relating to dimensional properties of individual cells is described below. Acquisition and analysis of data relating to dimensional properties may be achieved using the same or similar methods and apparatus described herein with reference to optical properties.

In sparsely populated cell samples, cell areas may be approximated using a single plane of focus. If it is desired to calculate volume, the z-axis (focus) can be automatically adjusted as well. For example, as an automated and controlled stage moves, the optically transparent container containing the sample population is positioned so that a series of data sets for multiple, spatially resolved areas of interest can be acquired, each image being acquired at a predetermined focal plane. The volume for each z-plane can be approximated (see algorithm below) and then the volumes for each z-coordinate added together.

General techniques for approximating cell areas and volumes, based on Doughty, S., "Calculating property for solids of revolution," *Machine Design*, pp 184–186, Dec. 10, 1981, are described below. These techniques are based on Green's theorem $$\int (Pdx + Qdy) \quad \int\int \left(\frac{\partial Q}{\partial x} - \frac{\partial P}{\partial y}\right) dx dy$$

(boundary) \qquad (area)

Individual cells are examined using an appropriate magnifying device. Edge detection of cell boundaries is achieved using, for example, a Sobel operator. The boundary is approximated by fitting it to a plurality of straight line segments of "n" line segments by "n" nodes. The integration of the boundary may be taken as "n" line integrals as follows:

$$\int_\Gamma (...) ds = \int_{x_1, Y_1}^{x_2, Y_2} (...) ds + \int_{x_2, Y_2}^{x_3, Y_3} (...) ds + ... + \int_{x_n, Y_n}^{x_1, Y_1} (...) ds$$

There are three cases:

Case 1: a vertical line, x=constant;

Case 2: a horizontal line, y=constant;

Case 3: an inclined line, $y=5_i (x-x_i)+y_i$

The area is thus:

$A = \int\int_A \cdot 1 \, dxdy$

To apply Green's theorem, the integral can be considered in the form of $\delta Q/\delta x - \delta P/\delta y$ and appropriate functions can be devised, e.g., $P(x, y)$ and $Q(x, y)$. For an area calculation, consider $Q(x, y)=0$ so that $\cdot Qdy=0$, and let $P=-y$ so that $\delta P/\delta y=-1$. Then, the area can be calculated as follows:

$$A = \int\int 1 dx dy = -\int\int \delta P/\delta y dx dy \qquad \text{(Green's Theorem)}$$

$$= \int\int (2Q/\delta x - \delta P/\delta y) dx dy$$

$$= \int (pdx + Qdy)$$

-continued $$= \int P dx$$

$$= -\int y dx$$

Case 2: $\Delta A = -y_i(x_{i+1}-x_i)$ Case 1=0
Case 3: $\Delta A = -[\frac{1}{2}5_i(x^2_{i+1}-x_i^2)+(y_i-5_ix_i)(x_{i+1}-x_i)]$ $A=\Sigma \Delta A$ For volume calculations, conventional edge detection using, for example, a Sobel operator, can be used to focus through an individual cell, which can be divided into a plurality (n) of individual, planar sections. The volume for each of the "n" sections can be calculated as $\Delta V_i = \Delta z_i \cdot \Delta A$; and the volume of the entire cell can be approximated as: $V=\Sigma \Delta V_i$. The determination and comparison of cell areas and volumes is preferably accomplished using computer hardware and/or software implementations.

According to another embodiment, methods and systems of the present invention acquire and compare data representative of one or more optical properties of individual cells or areas of interest in cell sample populations. Changes in optical properties that are indicative of physiological activity and that may be detected include, for example, reflection, refraction, diffraction, absorption, scattering, birefringence, refractive index, Kerr effect, and the like. Changes in optical properties are detected directly using photon sensitive elements and, optionally, optical elements that enhance the detected optical properties.

High resolution detection of dynamic geometrical and optical properties indicative of physiological activity may be accomplished with or without using dyes or other types of contrast enhancing agents according to the methods and apparatus of the present invention, as evidenced by the examples described herein. Many of the assessment techniques and apparatus of the present invention are physiologically noninvasive, in that detection and analysis of geometrical and/or intrinsic optical information does not require direct contact of the area of interest with any agents such as dyes, oils, devices, or the like. For particular applications, it may, however, be useful to administer contrast enhancing agents or dyes, probes, markers or the like, that amplify differences in an optical property as a function of physiological activity prior to acquiring subsequent data and generating a comparison. The use of contrast enhancing agents is described in detail, with reference to optical imaging of tumor and non-tumor tissue, in U.S. Pat. No. 5,465,718 and U.S. Pat. No. 5,438,989, which are incorporated by reference herein in their entireties. Suitable contrast enhancing agents include fluorescent and phosphorescent materials, dyes that bind to cell membranes, optical probes that preferentially accumulate in blood or in the intracellular space, phase resonance dye pairs, and the like. Detectors appropriate for use with such contrast enhancing agents are well known in the art.

Numerous devices for acquiring, processing and displaying data representative of one or more geometrical and/or optical properties of a cell sample population in culture or an area of interest in situ in an animal model may be employed. One preferred device is a camera that acquires images of one or more areas of interest at predetermined time intervals that can be compared to identify areas of changes in geometrical and/or optical properties that indicate physiological activity or dysfunction. The data acquisition device preferably incorporates or is used in conjunction with a device that magnifies the area of interest, such as a microscope.

Magnification sufficient to provide resolution of individual cells is preferred. An inverted microscope such as a Nikon Diophot 300 is suitable. For high throughput screening techniques using cell sample populations maintained under culture conditions, samples in optically transparent containers such as flasks, plates and multi-well plates, may be placed on an automated stage that is controlled and moved in a programmed fashion to permit periodic examination of individual cells or cell populations according to a programmed schedule. For example, a multi-well culture plate having a plurality of cell samples may be placed on an automated and controllable microscope stage. The stage is controlled by an automated microcontroller so that it automatically moves into position over each culture well. A data set relating to geometrical and/or optical properties of individual cells or a cell population is acquired for each position. In this manner, the system can rapidly and systematically acquire data corresponding to many samples. The physiological environment in selected wells may be altered by exposure to a physiological challenge, test agent or test condition, and the system may continue to automatically acquire data from the same wells in each culture plate at predetermined time intervals following treatment, with data acquired from various treatment wells being compared to data acquired from various control wells or empirically determined controls.

Acquisition of data representative of one or more geometrical and/or optical properties preferably provides high spatial resolution as well, so that geometrical or optical data corresponding to a particular spatial location is acquired at various time intervals for comparison. In this fashion, data acquired from single cells or highly localized areas of interest in cell sample populations is compared to provide reliable and highly-sensitive information concerning the physiological state or condition of the sample population. High spatial resolution is provided, for example, by implementing high resolution cameras and charge coupled devices (CCDs). Apparatus suitable for obtaining such images have been described in the patents incorporated herein by reference and are more fully described below. The optical detector preferably provides images having a high degree of spatial resolution at a magnification sufficient to detect single cells. Several images may be acquired at predetermined time intervals and combined, such as by averaging, to provide images for comparison.

Various data processing techniques may be advantageously used to assess the data collected in accordance with the present invention. Comparison data may be assessed or presented in a variety of formats. Processing may include averaging or otherwise combining a plurality of data sets to produce control, subsequent and various comparison data sets. Data may be converted from an analog to a digital form for processing, and back to an analog form for display as an image. Alternatively, data may be acquired, processed, analyzed, and output in a digital form.

Data processing may also include amplification of certain signals or portions of a data set (e.g., areas of an image) to enhance the contrast seen in data set comparisons, and to thereby identify cells or cell populations undergoing changes in geometrical and/or optical properties with a high degree of spatial resolution. For example, according to one embodiment, images are processed using a transformation in which image pixel brightness values are remapped to cover a broader dynamic range of values. A "low" value may be selected and mapped to zero, with all pixel brightness values at or below the low value set to zero, and a "high" value may be selected and mapped to a selected value, with all pixel brightness values at or above the high value mapped to the high value. Pixels having an intermediate brightness value, representing the dynamic changes in brightness indicative of neuronal activity, may be mapped to linearly or logarithmically increasing brightness values. This type of processing manipulation is frequently referred to as a "histogram stretch" and can be used according to the present invention to enhance the contrast of data sets, such as images, representing changes in neuronal activity.

Data processing techniques may also be used to manipulate data sets to provide more accurate combined and comparison data. For example, for in vivo applications, movement, respiration, heartbeat, seizure or reflex activity may shift an area of interest during data acquisition. It is important that corresponding data points in data sets are spatially resolved and precisely aligned to provide accurate combined and comparison data. Optical markers may be fixed at an area of interest and detected as the data is collected to aid in manual alignment or mathematical manipulation of data sets. Various processing techniques are described below and in the patents incorporated herein by reference.

Comparison data may be displayed in a variety of ways. Comparison data may be displayed, for example, in a graphical format that highlights geometrical or optical differences indicative of physiological changes. A preferred technique for presenting and displaying comparison data is in the form of visual images or photographic frames corresponding to spatially resolved areas of interest. This format provides a visualizable spatial location (two- or three-dimensional) of a cell population being analyzed. To enhance and provide better visualization of high contrast areas indicating changes in geometrical and/or optical properties indicative of physiological activity or dysfunction, comparison data may be processed to provide an enhanced contrast grey scale or even a color image. A look up table ("LUT") may be provided, for example, that converts the grey scale values for each pixel to a different (higher contrast) grey scale value, or to a color value. Color values may map to a range of grey scale values, or color may be used to distinguish between positive-going and negative-going geometrical or optical changes. In general, color-converted images provide higher contrast images that highlight changes in optical properties representing physiological activity, function or dysfunction.

Systems of the present invention generally comprise an illumination source for illuminating the biological material, an optical detector for acquiring data relating to a geometrical or optical property of the biological material, and data storage and analysis and output device(s) for storing data relating to a geometrical or optical property of the biological material, comparing various data sets, and/or control data profiles, to generate comparison data relating to changes in geometrical and/or optical properties indicative of changes in the physiological state of sample populations and to provide or display the output data in a useful format.

An emr source is used for illuminating an area of interest during acquisition of data representing one or more dimensional or intrinsic optical properties of cells or tissue at an area of interest. The emr source may be utilized to illuminate an area of interest directly, as when in vitro cell cultures maintained in optically transparent containers are illuminated or when tissue is exposed, such as in connection with surgery, or it may be utilized to illuminate an area of interest indirectly through adjacent or overlying tissue such as bone, dura, skin, muscle and the like. The emr source employed in the present invention may be a high or low intensity source, and may provide continuous or non-continuous illumination. Suitable illumination sources include high and intensity sources, broad spectrum and non-chromatic sources, tungsten-halogen lamps, lasers, light emitting diodes, laser diodes, and the like. Polarized light sources and dark field illumination techniques may also be used. Cutoff filters for selectively passing all wavelengths above or below a selected wavelength may be employed. A preferred cutoff filter excludes all wavelengths below about 695 nm Preferred emr wavelengths for acquiring data relating to intrinsic optical signals include, for example, wavelengths of from about 450 nm to about 2500 nm, and most preferably, wavelengths of the near infrared spectrum of from about 700 nm to about 2500 nm. Generally, longer wavelengths (e.g., approximately 800 nm) are employed to detect cellular or tissue condition of locations beneath the surface of cells or tissue, or beneath other materials such as skin, bone, dura, and the like. cortical activity. Selected wavelengths of emr may also be used, for example, when various types of contrast enhancing agents are administered. The emr source may be directed to the area of interest by any appropriate means. For some applications, the use of optical fibers is preferred. One preferred arrangement provides an emr source through strands of fiber optic using a beam splitter controlled by a D.C. regulated power supply (Lambda, Inc.).

The optical detection methods of the present invention may also usefully employ non-continuous illumination and detection techniques. For example, short pulse (time domain), pulsed time, and amplitude modulated (frequency domain) illumination sources may be used in conjunction with suitable detectors (see, Yodh, A. and Chance, B., *Physics Today*, March, 1995). Frequency domain illumination sources typically comprise an array of multiple source elements, such as laser diodes, with each element modulated at 180° out of phase with respect to adjacent elements (see, Chance, B. et al., *Proc. Natl. Acad. Sci. USA*, 90:3423–3427, 1993). Two-dimensional arrays, comprising four or more elements in two orthogonal planes, can be employed to obtain two-dimensional localization information. Such techniques are described in U.S. Pat. Nos. 4,972,331 and 5,187,672 which are incorporated by reference herein in their entireties.

Time-of-flight and absorbance techniques (Benaron, D. A. and Stevenson, D. K., *Science* 259:1463–1466, 1993) may also be usefully employed in the present invention. In yet another embodiment of the present invention, a scanning laser beam may be used in conjunction with a suitable detector, such as a photomultiplier tube, to obtain high resolution data images, preferably in the form of an area of interest.

Illumination with a part of the infrared spectrum allows for detection of intrinsic optical signals through tissue overlying or adjacent the area of interest, such as dura and skull. One exemplary infrared emr source suitable for detection of intrinsic optical signals through tissue overlying or adjacent the area of interest is a Tunable IR Diode Laser from Laser Photonics, Orlando, Fla. When using this range of far infrared wavelengths, the optical detector is preferably provided as an infrared (IR) detector. IR detectors may be constructed from materials such as indium arsenide, germanium and mercury cadmium telluride, and are generally cryogenically cooled to enhance their sensitivity to small changes in infrared radiation. One example of an IR detection system which may be usefully employed in the present invention is an IRC-64 infrared camera (Cincinnati Electronics, Mason, Ohio).

The area of interest is preferably evenly illuminated to effectively adjust the signal over a full dynamic range, as described below. Nonuniformity of illumination is generally caused by fluctuations of the illumination source and intensity variations resulting from the three-dimensional nature of the tissue surface. More uniform illumination can be provided over the area of interest, for example, by using diffuse lighting, mounting a wavelength cutoff filter in front of the optimal detector and/or emr source, or combinations thereof. Fluctuation of the illumination source itself is preferably prevented by using a light feedback mechanism to regulate the power supply of the illumination source. In addition, a sterile, optically transparent plate may contact and cover an area of interest to provide a flatter, more even contour surface for detection. Fluctuations in illumination can be compensated for using detection processing algorithms, including placing a constant shade grey image marker point at the area of interest as a control point.

The system also comprises an optical detector for acquiring a signal representative of one or more optical properties of the area of interest. Any photon detector may be employed as an optical detector. Suitable optical detectors include, for example, photo diodes, photo multiplier tubes, photo sensitive silicon detector chips, such as those provided in CCD devices, and the like. Multiple emr sources and/or multiple photon detectors may be provided and may be arranged in any suitable arrangement. Specialized detectors for detecting selected optical properties may be employed. One preferred optical detector for acquiring data in the format of an analog video signal is a CCD video camera which produces an output video signal at 30 Hz having, for example, 512 horizontal lines per frame using standard RS 170 convention. One suitable device is a CCD-72 Solid State Camera (Dage-MTI Inc., Michigan City, Ind.). Another suitable device is a COHU 6510 CCD Monochrome Camera with a COHU 6500 electronic control box (COHU Electronics, San Diego, Calif.). In some cameras, the analog signal is digitized 8-bits deep on an ADI board (analog-to-digital board). The CCD may be cooled, if necessary, to reduce thermal noise.

Data processing is an important feature of the optical detection and analysis techniques and systems of the present invention. In use, for example, a CCD apparatus is preferably adjusted (at the level of the analog signal and before digitizing) to amplify the signal and spread the signal across the full possible dynamic range, thereby maximizing the sensitivity of the apparatus. Specific methods for detecting optical signals with sensitivity across a full dynamic range are described in detail in the patents incorporated herein by reference. Means for performing a histogram stretch of the difference frames (e.g., Histogram/Feature Extractor HF 151–1-V module, Imaging Technology, Woburn, Mass.) may be provided, for example, to enhance each difference image across its dynamic range. Exemplary linear histogram stretches are described in Green, *Digital Image Processing: A Systems Approach*, Van Nostrand Reinhold: New York, 1983. A histogram stretch takes the brightest pixel, or one with the highest value in the comparison image, and assigns it the maximum value. The lowest pixel value is assigned the minimum value, and every other value in between is assigned a linear value (for a linear histogram stretch) or a logarithmic value (for a log histogram stretch) between the maximum and minimum values. This allows the comparison image to take advantage of the full dynamic range and provide a high contrast image that clearly identifies areas of neuronal activity or inactivity.

Noise (such as 60 Hz noise from A.C. power lines) is filtered out in the control box by an analog filter. Additional adjustments may further enhance, amplify and condition the analog signal from a CCD detector. One means for adjusting the input analog signal is to digitize this signal at video speed (30 Hz), and view the area of interest as a digitized image that is subsequently converted back to analog format.

It is important that data, such as consecutive data sets corresponding to a particular area of interest, be aligned so that data corresponding to the same spatially resolved location is compared. If data sets are misaligned prior to comparison, artifacts are introduced and the resulting comparison data set may amplify noise and edge information. Data misalignment may be caused by sample movement or motion, heartbeat, respiration, and the like. Large movements of cells in an area of interest being analyzed may require a new orientation of the detector. It is possible to compensate for small movements of cells in the area of interest by either mechanical or computational means, or a combination of both.

Real-time motion compensation and geometric transformations may also be used to align corresponding data. Simple mechanical translation of data or more complex (and generally more accurate) geometric transformation techniques can be implemented, depending upon the input data collection rate and amount and type of data processing. For many types of image data, it is possible to compensate by a geometrical compensation which transforms the images by translation in the x-y plane. In order for an algorithm such as this to be feasible, it must be computationally efficient (preferably implementable in integer arithmetic), memory efficient, and robust with respect to changes in ambient light.

For example, functional control points or numbers can be located in an area of interest and triangulation-type algorithms used to compensate for movements of these control points. Goshtasby ("Piecewise Linear Mapping Functions for Image Registration," *Pattern Recognition* 19:459–66, 1986) describes a method whereby an image is divided into triangular regions using control points. A separate geometrical transformation is applied to each triangular region to spatially register each control point to a corresponding triangular region in a control image.

"Image warping" techniques may be employed whereby each subsequent image is registered geometrically to the averaged control image to compensate for movement. Image warping techniques (described in, for example, Wolberg, *Digital Image Warping*, IEEE Computer Society Press: Los Alamitos, Calif., 1990), may be used. Image warping techniques can further indicate when movement has become too great for effective compensation and a new averaged control image must be acquired.

The data storage processing and analysis function is generally performed and controlled by a host computer. The host computer may comprise any general computer (such as an IBM PC type with an Intel 386, 486, Pentium or similar microprocessor or Sun SPARC) that is interfaced with the emr source and/or optical detector and controls data acquisition and flow, comparison computations, analysis, output, and the like. The host computer thus controls acquisition and analysis of data and provides a user interface.

The host computer may comprise a single-board embedded computer with a VME64 interface, or a standard (IEEE 1014–1987) VME interface, depending upon bus band width considerations. Host computer boards which may be employed in the present invention include, for example, Force SPARC/CPU-2E and HP9000 Model 7471. The user interface can be, for example, a Unix/X-Window environment. The image processing board can be, for example, based upon Texas Instruments' MVP and other chips to provide real-time image averaging, registration and other processing necessary to produce high quality difference images for intraoperative viewing. This board will also drive a 120×1024 RGB display to show a sequence of difference images over time with pseudo-color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, the light source and optical detector control box.

A real-time data acquisition and display system, for example, may comprise four boards for acquisition, image processing, peripheral control and host computer. A minimal configuration with reduced processing capabilities may comprise just the acquisition and host computer boards. The acquisition board comprises circuitry to perform real-time averaging of incoming video frames and allow readout of averaged frames at a maximum rate bus. A VME bus is preferred because of its high peak bandwidth and compatibility with a multitude of existing VME products. The acquisition board should also support many different types of optical detectors via a variable scan interface. A daughter board may support the interfacing needs of many different types of optical detectors and supply variable scan signals to the acquisition motherboard. Preferably, the unit comprises a daughter board interfacing to an RS-170A video signal to support a wide base of cameras. Other camera types, such as slow scan cameras with a higher spatial/contrast resolution and/or better signal to noise ratio, can be developed and incorporated in the inventive device, as well as improved daughter boards to accommodate such improved cameras.

Data relating to dimensional and/or intrinsic optical properties of a sample population acquired, for example, as analog video signals, may be continuously processed using, for example, an image analyzer (e.g., Series 151 Image Processor, Imaging Technologies, Inc., Woburn, Mass.). An image analyzer receives and digitizes an analog video signal with an analog to digital interface and performs at a frame speed of about $\frac{1}{30}$th of a second (e.g. 30 Hz or "video speed"). Processing the signal involves first digitizing the signal into a series of pixels or small squares assigned a value (in a binary system) dependent upon the number of photons (i.e., quantity of emr) being reflected off tissue from the part of the area of interest assigned to that pixel. For example, in a standard 512×512 image from a CCD camera, there would be 262,144 pixels per image. In an 8 bit system, each pixel is represented by 8 bits corresponding to one of 256 levels of grey.

The signal processor may include a programmable lookup table (e.g., CM150-LUT16, Imaging Technology, Woburn, Mass.) initialized with values for converting grey coded pixel values, representative of a black and white image, to color coded values based upon the intensity of each grey coded value. Using image stretching techniques, the highest and lowest pixel intensity values representing each of the pixels in a digital image frame are determined over a region of the image frame which is to be stretched. Stretching a selected region over a larger range of values permits, for example, easier identification and removal of relatively high, spurious values resulting from noise.

The signal processor means may further include a plurality of frame buffers having frame storage areas for storing frames of digitized image data received from the A/D interface. The frame storage area comprises at least one megabyte of memory space, and preferably at least 8 megabytes of storage space. An additional 16-bit frame storage area may be provided as an accumulator for storing processed image frames having pixel intensities represented by more than 8 bits. The processor means preferably includes at least three frame buffers, one for storing the averaged control image, another for storing the subsequent image, and a third for storing a comparison image.

The signal processor may further comprise an arithmetic logic unit (e.g., ALU-150 Pipeline Processor) for performing arithmetical and logical functions on data located in one or more frame buffers. An ALU may, for example, provide image (data) averaging in real time. A newly acquired digitized image may be sent directly to the ALU and combined with control images stored in a frame buffer. A 16 bit result can be processed through an ALU, which will divide this result by a constant (i.e., the total number of images). The output from the ALU may be stored in a frame buffer, further processed, or used as an input and combined with another image.

Normally, areas of increased physiological activity exhibit an increase of the emr absorption capacity of the cell sample or tissue (i.e., the cell sample gets darker if visible light is used for emr illumination, or an intrinsic signal increases in a positive direction). Similarly, a reduction in physiological activity generally corresponds to a decrease of emr absorption capacity of the tissue (i.e., the tissue appears brighter, or intrinsic signals become negative). For example, data set A is a subsequent averaged image and data set B is an averaged control image. Normally, when a pixel in data set A is subtracted from a pixel in data set B and a negative value results, this value is treated as zero. Hence, difference images cannot account for areas of inhibition. The present invention provides a method for identifying both negative and positive intrinsic signals, by: (a) subtracting data set A (a subsequent averaged image) from data set B (an averaged control image) to create a first difference data set, whereby all negative pixel values are zero; and (b) subtracting data set B from data set A to create a second difference data set whereby all negative pixel values are zero; and adding the first and second difference data sets to create a "sum difference data set." The sum difference data set shows areas of increased activity (i.e., color coded with warmer colors such as yellow, orange, red) and may be visualized as image areas of less activity or inhibition (i.e., color coded with colder colors such as green, blue, purple). Alternatively, one can overlay the first difference data set on the second difference data set. The difference output may be visualized as an image and may be superimposed on the real time analog image to provide an image of the area of interest (e.g., cortical surface) superimposed with a color-coded difference frame to indicate where there are intrinsic signals in response to a challenge, stimulus, paradigm, or the like.

The comparison (e.g., difference) data may be further processed to smooth out the data and remove high frequency noise. For example, a lowpass spatial filter can block high spatial frequencies and/or low spatial frequencies to remove high frequency noises at either end of the dynamic range. This provides a smoothed-out processed difference data set (in digital format). The digitally processed difference data set can be provided as an image and color-coded by assigning a spectrum of colors to differing shades of grey. This image may then be converted back to an analog image (by an ADI board) and displayed for a real time visualization of differences between an averaged control image and subsequent images. Moreover, the processed difference image can be superimposed over the analog image to display specific tissue sites where a contrast enhancing agent may have a faster uptake, or where an intrinsic signal may be occurring.

Processing speed may be enhanced by adding a real time modular processor or faster CPU chip to the image processor. One example of a real time modular processor which may be employed in the present invention is a 150 RTMP-150 Real Time Modular Processor (Imaging Technology, Woburn, Mass.). The processor may further include an optical disk for storing digital data, a printer for providing a hard copy of the digital and/or analog data and a display, such as a video monitor, to permit the user to continuously monitor the comparison data output.

A single chassis may house all of the modules necessary to provide optical detection and analysis in a format that can be easily interpreted, such as an image format, according to the present invention. The necessary components, whether or to whatever degree integrated, may be installed on a rack that is easily transportable, along with display monitors and peripheral input and output devices.

A preferred high resolution and high performance system comprising a PentaMAX 576×384FT LCD system (by Princeton Instruments Inc., N.J.) digitizes the data at the chip and provides a large dynamic range and reduced noise. This system may be interfaced using a PCI-bus to a dual-400 Mhz Pentium PC running windows NT. Image analysis algorithms may be written in C using Microsoft VisualC++ Version 5.0 compiler. For more rapid online processing, the data may be routed to dedicated imaging hardware residing in the PC computer. For example, IM-PCI hardware (by Imaging Technology Inc., Bedford, Mass.) could be used. One such configuration would consist of the following IM-PCI boards and modules: IM-PCI, AMVS, and a CMALU.

The imaging methods applied to in vivo applications may acquire data at the surface of an area of interest. As described above, longer wavelengths of emr (in the infrared range) can be used to image areas of interest which are deeper in tissue or below overlying tissue. In some areas of the body longer wavelength visible light and near infrared emr can easily pass through such tissue for imaging. Moreover, if a difference image is created between the image acquired at 500 nm emr and the image acquired at 700 nm emr, the difference image will show an optical slice of tissue. Administration of an imaging agent which absorbs specific wavelengths of emr can act as a tissue filter of emr to provide a filter in the area of interest. In this instance, it is desirable to utilize an imaging agent that remains in the tissue for a prolonged period of time.

In a simple system suitable for assessing cell populations in vivo in animal or tissue culture models, the systems of the present invention may include one or more optical fiber(s) operably connected to an emr source that illuminates cells or tissue, and another optical fiber operably connected to an optical detector, such as a photodiode, that detects one or more optical properties of the illuminated cells or tissue. The detector may be used to acquire obtain control data representing the "normal" or "background" optical properties of a sample population, and then to acquire subsequent data representing the optical properties of the sample population during or following administration of a test agent or test condition. A physiological challenge and/or a stimulus that stimulates a disease or pathological state may be administered prior to administration of the treatment agent or condition. The system comprises or is in communication with a data storage and processing system having information storage and processing capability sufficient to compare the geometrical and/or optical properties of individual cells or cell samples to empirically determined standards, or to data acquired at different points in time.

In operation, an area of interest in an in vitro or in vivo cell sample is illuminated with electromagnetic radiation (emr) and one or a series of data points or data sets representing one or more geometrical and/or optical properties of a spatially resolved area of interest is acquired during an interval of "normal" physiological activity. This data represents a control, or background data profile for that particular cell sample under those particular physiological conditions. A series of data sets is preferably combined, for example by averaging, to obtain a control data profile. The control data profile is stored for comparison with other data sets. Similarly, control data sets may be collected and stored that represent a background data profile for particular cell types under specified physiological conditions.

Data sets representing the corresponding geometrical and/or optical property of the sample population at the same, spatially resolved areas of interest, are acquired during a subsequent time period. For monitoring applications, data may be collected at regular time intervals to monitor the condition of the cell sample and to detect aberrations from the baseline profile. For screening applications, one or more subsequent data set(s) is collected during a period following physiological activity or inhibition, induced, for example, by introduction of a test compound or by exposure to a test condition. Physiological activity or inhibition may be induced by a "natural" occurrence such as a seizure or stroke in an animal model, or it may be induced by administering a paradigm or an agent to an in vitro or in vivo cell sample to stimulate changes in geometrical and/or optical properties of the cell sample that are indicative of physiological activity or inhibition. During a monitoring interval or stimulation of an intrinsic physiological response, one or a series of subsequent data sets, representing one or more of the detected geometrical or optical properties of the area of interest, is acquired. A series of subsequent data sets is preferably combined, for example by averaging, to obtain a subsequent data set. The subsequent data set is compared with the control data set to obtain a comparison data set, preferably a difference data set. Comparison data sets are then analyzed for evidence of changes in geometrical and/or optical properties representative of physiological activity or inhibition within the area of interest.

FIG. 1 shows a schematic flow diagram illustrating an exemplary system, as well as exemplary output data of the present invention with reference to in vitro cell populations. A cell population may comprise cells in suspension at a sparse cell density, or confluent layers of cells, or layers of cells at other predetermined cell densities, or a tissue sample, such as a tissue slice. Maintenance of a wide variety of cell and tissue samples under cell culture conditions is well known in the art.

The sample population is placed at a predetermined location on a platform, such as on a microscope stage. In the example shown in FIG. 1, the sample is an acute rat hippocampal slice maintained in a submerged perfusion chamber. Alternatively, the sample may be cell samples maintained in cell culture media in flasks, multiple well plates, and the like. Multiple well tissue culture plates may be used for high throughput screening, in combination with an automated stage for positioning cell samples in individual wells for optical detection at predetermined intervals. Programmable, automated positioning devices are well known in the art.

An optical detector (in this case, a CCD camera) is attached to the camera-port of the microscope. During one or more control period(s) and one or more test period(s), data relating to dimensional and/or optical properties of individual cells or of an area of interest in the cell sample are acquired, stored and processed. Acquisition and processing of data may be accomplished as described below and in the Examples.

The grey-scale image on the upper right is the unprocessed image of the tissue-slice as viewed by the CCD camera. This slice was then electrically stimulated at two different intensities: a low-intensity electrical stimulus causing a small increase in neuronal and synaptic activation; and a high-intensity electrical stimulus causing a larger increase in neuronal and synaptic activity.

The Stim-Control image was generated as described below in Example 1. Briefly, an image acquired during the electrical stimulation was subtracted from an image acquired in the control state. This image was then filtered with a low-pass filter, histogram-stretched, and contrast enhanced. Images may be pseudo-colored to indicate intensity of activity-evoked optical change (arrow on color-bar).

The dynamic optical changes represented in these images can also be plotted as a graph (lower right image). Here, each data-point represents the average change in light-transmission through the small box indicated on the contrast enhanced image. A series of images, two seconds apart, were acquired and the average value was calculated for each image and plotted as a point on the graph. The tissue was electrically stimulated for two seconds at the points indicated by the straight lines. The small peak indicates the maximum optical change induced by the first small electrical stimulation, the larger peak from the second larger stimulus. The electrical stimulation was ceased after two seconds and the tissue was allowed to recover. The plots of the recovery are characteristic of the ion-homeostatic mechanisms of the tissue. Their recovery could be quantified, for example, by finding the best exponential fits for the recovery periods.

Methods and systems of the present invention are well-suited for high throughput screening of libraries of compounds, and combinations of compounds, to identify candidate compounds and combinations having desired therapeutic or diagnostic properties. In one approach, well established agents, such as therapeutic agents effective in treating various conditions are identified; modifications to the therapeutic agent(s) are made, for example, analog and derivative compounds are identified and synthesized; and the modified agents are then screened for efficacy under various conditions using screening techniques of the present invention. In a similar fashion, combinations of therapeutic compounds, combinations of a therapeutic compound with candidate agents, and combinations of candidate agents may be screened for efficacy under certain conditions using screening techniques of the present invention.

Numerous agents are known for treatment of various conditions, such as cancers and other proliferative disorders, psychiatric and neurological disorders, chronic pain, and various other conditions. In one approach, such agents may be screened using techniques of the present invention. Modifications to such agents may then be made, for example, using combinatorial chemistry and molecular modeling techniques, to produce modified candidate agents, which may be screened for various activities using methods of the present invention. Similarly, combinations of both known agents and modified agents may be screened using techniques of the present invention.

The present invention contemplates high throughput screening of agents for treating cancers and other proliferative disorders. The following agents, and modifications of the following agents, including analogs, derivatives, fragments, active moieties, and the like, may be screened using methods and systems of the present invention: AA (ara-C, Adriamycin); AAF (2-acetylaminofluorene); AAFC (flurocitabine); ABC (Adriamycin, BCNU, cyclophosphamide); ABCD (Adriamycin, bleomycin, CCNU and dacarbazine); ABCM (Adriamycin, bleomycin, cyclophosphamide, mitomycin-C); ABD (Adriamycin, bleomycin, DTIC); ABDIC (Adriamycin, bleomycin, dacarbazine, CCNU and prednisone); ABDV (Adriamycin, bleomycin, DTIC, vinblastine); ABLC (amphotericin B lipid complex); ABOS (doxorubicin, bleomycin sulfate, vincristine, streptozocin); ABP (Adriamycin, bleomycin, prednisone); ABPP (bropirimine); ABV (actinomycin-D, bleomycin, vincristine); ABV (Adriamycin, bleomycin, vinblastine); ABVD (Adriamycin, bleomycin, vincristine, dacarbazine); ABVE (Adriamycin, bleomycin, vincristine, etoposide); ABVP (Adriamycin, bleomycin sulfate, teniposide, prednisone); ABVP (Adriamycin, bleomycin sulfate, vinblastine, prednisone); ABVP (Adriamycin, bleomycin sulfate, vincristine, prednisone); AC (Adriamycin, carmustine); AC (Adriamycin, CCNU); AC (Adriamycin, cisplatin); AccuSite; Ac-D-Ac (Adriamycin, daunorubicin, Adriamycin); ACe (Adriamycin, cyclophosphamide); ACE (Adriamycin, cyclophosphamide, etoposide); ACFUCY (actinomycin D, 5-fluorouracil, cyclophosphamide); ACID (Adriamycin, cyclophosphamide, imidazole, dactinomycin); Acivicin; aclarubicin; aclarubicin HCl; ACM (Adriamycin, cyclophosphamide, methotrexate); ACNU (nimustine); ACOAP (Adriamycin, cyclophosphamide, Oncovin, cytosine arabinoside, prednisone); ACOP (Adriamycin, cyclophosphamide, Oncovin, prednisone); ACOPP (Adriamycin, cyclophosphamide, Oncovin, prednisone, procarbazine); ACR (aclarubicin); ACT (actinomycin); ACT-C (actinomycin-C); ACT-D (actinomycin-D); Actinex (masoprocol); actinomycin-D (ACT-D); ACT-FU-Cy (actinomycin-D, 5-FU, cyclophosphamide); ADBC (Adriamycin, DTIC, bleomycin, CCNU); ADE (ara-C, daunorubicin, etoposide); adenine arabinoside (Ara-A); ADIC (Adriamycin, DTIC); ADOC (Adriamycin, cisplatin, vincristine, cyclophosphamide); AdOAP (Adriamycin, Oncovin, ara-C, prednisone); AdOP (Adriamycin, Oncovin, prednisone); adozelesin; ADR-529; Adria+BCNU (Adriamycin+BCNU); Adriamycin PFS; Adriamycin RDF; Adria-L-PAM (Adriamycin, L-phenyl-alanine mustard); Adrucil (fluorouracil); AF 1890 (lonidamine); AFM (Adriamycin, 5-fluorouracil, methotrexate); AGT (aminoglutethimide); Agrelin (anagrelide); AID (Adriamycin, ifosfamide, dacarbazine, mesna); AIM (L-asparaginase, ifosfamide, methotrexate); AL-721; aldesleukin (Proleukin); alfa-2 or 26 interferon; alfacalcidol (One-Alpha); Alferon LDO; interferon alfa-n3); Alferon-N (interferon alfa-n3); Alkaban-AQ (vinblastine); Alkeran (melphalan); all trans-retinoic acid (Tretinoin); Allergan 211 (idoxuridine); ALOMAD (Adriamycin, Leukeran, Oncovin, methotrexate, actinomycin D, dacarbazine); Alpha-Beta (alpha tocopherol and beta carotene); Alpha Chymar (alpha-chymotrypsin); alpha interferon (IFN-A); alphal-antitrypsin; alpha-2 interferon(IFN-alpha-2); 5-alpha reductase inhibitors; alpha-TGI (teroxirone); AlphaNine; ALTO (afterloading tandem and ovoids); ALT-RCC (autolymphocyte-based treatment for renal cell carcinoma); altretamine (Hexalen, Hexastat); AmBisome; amethopterin (methotrexate); amiloride (Midamor); 9-aminocamptothecin; aminoglutethimide (Cytadren, AGT, Elipten); aminopterin; aminothiadiazole; AML-2-23 monoclonal antibody; AMMEN-OE5 monoclonal antibody;

amonafide (nafidimide); amphotericin B colloidal dispersion (ABCD); amphotericin B lipid complex (ABLC); Ampligen (polyribonucleotide); AMSA (amsacrine); amsacrine (m-AMSA, AMSA, Amsidyl); Amsidyl (amsacrine); anakinra (Antril); anagrelide (Agrelin); ANAN (anandron); anandron (nilutamide); anastrozole (Arimidex); Andro-Cyp; Android-F (Note: Discontinued in 1991); Andronaq (Note: Discontinued in 1991); Andronate (testosterone cypionate); Andropository (testosterone enanthate); Andryl (testosterone); annamycinLF (liposomal annamycin); anthramycin (also antramycin); anthrapyrazole; anti-B4-blocked ricin; anti-EGFR (RG 838520); anti-MY9-blocked ricin; anti-T12 allogeneic BMT; anti-TAP-72 immunotoxin; Antril (anakinra); AOPA (ara-C, Oncovin, prednisone, asparaginase); AOPE (Adriamycin, Oncovin, prednisone, etoposide); APC (AMSA, prednisone, chlorambucil); APE (Adriamycin, Platinol, etoposide); APE (ara-C, Platinol, etoposide); APO (Adriamycin, prednisone, Oncovin); AR-623 (liposomal Tretinoin); ara-A (adenine arabinoside); ara-AC (azacytosine arabinoside) (fazarabine); arabinofuranosylcytosine (cytarabine); arabinosyl cytosine (cytarabine); ara-C (cytosine arabinoside) (cytarabine); ara-C+ADR (cytarabine, Adriamycin); ara-C+DNR+PRED+MP (cytarabine, daunorubicin, prednisolone, mercaptopurine); ara-C+6TG (cytarabine, thioguanine); ara-C-HU (ara-C, hydroxyurea); Ara-Cytidine (cytarabine); ara-G; Aredia (pamidronate disodium); Arensin (fadrozole); Arimidex (anastrozole); Arotinoid; ASHAP (Adriamycin, Solu-Medrol, high-dose ara-C, Platinol); ASHAP/BACOS; ASN (L-asparaginase); ASP (L-asparaginase); asparaginase (Elspar); ATG (antithymocyte globulin); Atzpodien regimen for renal cell carcinoma; autolymphocyte therapy, AV (Adriamycin, vincristine); AVAD (doxorubicin, vincristine, cytarabine, dexamethasone); Avicidin; AVM (Adriamycin, vinblastine, methotrexate); AVM (Adriamycin, vincristine, mitomycin-C); AVP (actinomycin D, vincristine, Platinol); AVP (Adriamycin, vincristine, procarbazine); azacitidine; 5-azacitidine (Mylosar); azathioprine (Imuran); AZC (azacitidine); aziridinylbenzoquinone (diaziquone); AZQ (aziridinylbenzoquinone); BAC (BCNU, cytarabine, cyclophosphamide); Bacatin III; BACO (bleomycin, Adriamycin, CCNU, Oncovin); BACOD (bleomycin, Adriamycin, cyclophosphamide, Oncovin, dexamethasone); BACON (bleomycin, Adriamycin, CCNU, Oncovin, nitrogen mustard); BACOP (bleomycin, Adriamycin, cyclophosphamide, Oncovin, prednisone); BACT (BCNU, ara-C, cyclophosphamide, 6-thioguanine); BACT (bleomycin, Adriamycin, cyclophosphamide, tamoxifen); BAM/BLITZ (B4 blocked ricin); BAMON (bleomycin, Adriamycin, methotrexate, Oncovin, nitrogen mustard); BAP (bleomycin, Adriamycin, prednisone); BAPP (bleomycin, doxorubicin, cisplatin, prednisone); BAVIP (bleomycin, Adriamycin, vinblastine, imidazole carboxamide, prednisone); BBVP-M (BCNU, bleomycin, VePesid, prednisone, methotrexate); BCAP (BCNU, cyclophosphamide, Adriamycin, prednisone); BCAVe (bleomycin, CCNU, Adriamycin, Velban); BCD (bleomycin, cyclophosphamide, dactinomycin); BCG (bacillus Calmette-Guerin vaccine); B-CHOP (bleomycin Cytoxan, hydroxydaunomycin, Oncovin, prednisone); BCMF (bleomycin, cyclophosphamide, methotrexate, fluorouracil); BCNU (bis-chloronitrosourea) (carmustine); BCOP (BCNU, cyclophosphamide, Oncovin, prednisone); BCP (BCNU, cyclophosphamide, prednisone); BCVP (BCNU, cyclophosphamide, vincristine, prednisone); BCVPP (BCNU, cyclophosphamide, vinblastine, procarbazine, prednisone); BCVPP-bleo (BCNU, cyclophosphamide, vinblastine, procarbazine, bleomycin); BCX-34; B-DOPA (bleomycin, dacarbazine, Oncovin, prednisone, Adriamycin); BEAC (BCNU, etoposide, ara-C, cyclophosphamide); BEAM (BCNU, etoposide, cytarabine, melphalan); BEMP (bleomycin, Eldisine, mitomycin, Platinol); BEP (bleomycin, etoposide, Platinol); Betaseron (interferon beta-1); BHD (BCNU, hydroxyurea, dacarbazine); BHDV (BCNU, hydroxyurea, dacarbazine, vincristine); bicalutamide; BiCNU (carmustine); B-IFN (beta-interferon); Biodel Imiplant/BCNU; BioTropin; BIP (bleomycin, ifosfamide, Platinol); bisacetamide (heramethylene); bisantrene hydrochloride (Bisantrene); Bisantrene (bisantrene hydrochloride); bischlorethylnitrosurea (BCNU); bispecific antibody 520C9x22; bizelesin; Blenoxane (bleomycin); BLEO (bleomycin); BLEO-COMF (bleomycin, cyclophosphamide, Oncovin, methotrexate, fluorouracil); BLEO-MOPP (bleomycin, nitrogen mustard, Oncovin, procarbazine, prednisone); bleomycin (Blenoxane) (BLEO) (BLM); bleomycin HCl; bleomycin sulfate; BLITZ (monoclonal antibodies); BLM (bleomycin sulfate); BM-92103; B-MOPP (bleomycin, mechlorethamine, Oncovin, procarbazine, prednisone); BMP (BCNU, methotrexate, procarbazine); BMS-182248 (BR96-Dox); BMY-28090; BMY-45622; BOAP (bleomycin, Oncovin, Adriamycin, prednisone); BOLD (bleomycin, Oncovin, lomustine, dacarbazine); BOMP (bleomycin, Oncovin, Matulane, prednisone); BONP (bleomycin, Oncovin, Natulan, prednisolone); BOP (BCNU, Oncovin, prednisone); BOP (bleomycin, Oncovin, Platinol); BOPAM (bleomycin, Oncovin, prednisone, Adriamycin, mechlorethamine, methotrexate); BOPP (BCNU, Oncovin, procarbazine, prednisone); Borocell; BR-96 (doxorubicin monoclonal antibody immunoconjugate); brachytherapy; BRCA genetic testing; brequinar; brequinar sodium; BRL39123A; bromodeoxyuridine (BUdR); 5-bromodeoxyuridine (broxuridine or BUdR); 5-bromo-2-deoxyuridine; 5-bromouracil; bromfenac; bropirimine; broxuridine (BUdR); BSO (buthionine sulfoximine); BSRL (buserelin) (Suprefact); BT (BCNU, triazinate); BUdR (bromodeoxyuridine or broxuridine); BU (busulfan); BUS (busulfan, Myleran); buserelin (BSRL) (Suprefact); busulfan (BU, Myleran); buthionine sulfoximine (BSO); BVAP (BCNU, vincristine, Adriamycin, prednisone); BV-ara-U; BVCPP (BCNU, vinblastine, cyclophosphamide, procarbazine, prednisone); BVD (BCNU, vincristine, dacarbazine); BVDS (bleomycin, Velban, doxorubicin, streptozocin); BVPP (BCNU, vincristine, procarbazine, prednisone); BW 301 U (piritrexim); BW A770U (crisnatol mesylate); CA 15-3; CA 72-4; CA (cyclophosphamide, Adriamycin); CABOP, CA-BOP (cyclophosphamide, Adriamycin, bleomycin, Oncovin, prednisone); CABS (CCNU, Adriamycin, bleomycin, streptozocin); CAC (cisplatin, ara-C, caffeine); CACP (cisplatin); cactinomycin (actinomycin C); CAD (cyclophosphamide, Adriamycin, dacarbazine); CAD (cytosine arabinoside, daunorubicin); CADIC (cyclophosphamide, Adriamycin, DTIC); CAE (cyclophosphamide, Adriamycin, etoposide); CAP (cyclophosphamide, Adriamycin, 5-fluorouracil); CAFFI (cyclophosphamide, Adriamycin, 5-fluorouracil by continuous infusion); CAFP (cyclophosphamide, Adriamycin, 5-fluorouracil, prednisone); CAFTH (cyclophosphamide, Adriamycin, 5-fluorouracil, tamoxifen, Halotestin); CAFVP (cyclophosphamide, Adriamycin, 5-fluorouracil, vincristine, prednisone); CALF (cyclophosphamide, Adriamycin, leucovorin calcium, 5-fluorouracil); CALF-E; (cyclophosphamide, Adriamycin, leucovorin calcium, 5-fluorouracil, ethinyl estradiol); calusterone; CAM (cyclophosphamide, Adriamycin, methotrexate); CAMB (cyclophosphamide, Adriamycin, methotrexate, bleomycin); CAMELEON (cytosine arabinoside, high-dose methotrexate, leucovorin, Oncovin); CAMEO (cyclophosphamide, Adriamycin, methotrexate, etoposide, Oncovin); CAMF (cyclophosphamide, Adriamycin, methotrexate, 5-fluorouracil); CAMF (cyclophosphamide, Adriamycin methotrexate, folic acid); CAMLO (cytosine arabinoside, methotrexate, leucovorin, Oncovin); CAMP (cyclophosphamide, Adriamycin, methotrexate, procarbazine); Campath 1H; camptothecin-11 (CPT-11); CAO (cyclophosphamide, Adriamycin, Oncovin); CAP (cyclophosphamide, Adriamycin, Platinol); CAP (cyclophosphamide, Adriamycin, prednisone); CAP-I (cyclophosphamide, Adriamycin, Platinol); CAP-II (cyclophosphamide, Adriamycin, high-dose Platinol); CAP-BOP (cyclophosphamide, Adriamycin, procarbazine, bleomycin, Oncovin, prednisone); capromab pendetide; CAPPr (cyclophosphamide, Adriamycin, Platinol, prednisone); caracemide; carbetimer; carboplatin (Paraplatin); carboxamide; Cardioxane; carmustine (BCNU) (BiCNU); carubicin; carubicin HCl; carzelesin; Casodex; CAT (cytosine arabinoside, Adriamycin, 6-thioguanine); CAT (cytosine arabinoside, thioguanine); Catrix capsules and amp; injections; CAV (cyclophosphamide, Adriamycin, Velban); CAV (cyclophosphamide, Adriamycin, vincristine); CAVe, CA-Ve (CCNU, Adriamycin, Velban); CAVP (cyclophosphamide, Adriamycin, VM-26, prednisone); CAVP-I (cyclophosphamide, Adriamycin, vincristine, prednisone); CAVP-16 (cyclophosphamide, Adriamycin, VP-16); CAVPM (cyclophosphamide, Adriamycin, VP-16, prednisone, methotrexate); CB10-277; CPBBA (cyclophosphamide, bleomycin, procarbazine, prednisone, Adriamycin); CBV (cyclophosphamide, BCNU, VePesid); CBV (cyclophosphamide, BCNU, VP-16); CBVD (CCNU, bleomycin, vinblastine, dexamethasone); CC (carboplatin, cyclophosphamide); CC49 monoclonal antibody; CCAVV (CCNU, cyclophosphamide, Adriamycin, vincristine, VP-16); CCFE (cyclophosphamide, cisplatin, 5-fluorouracil, estramustine); CCM (cyclophosphamide, CCNU, methotrexate); CCMA (CCNU, cyclophosphamide, methotrexate, Adriamycin); CCNU (lomustine); CCNU-OP (CCNU, Oncovin, prednisone); CCOB (CCNU, cyclophosphamide, Oncovin, bleomycin); CCV (CCNU, cyclophosphamide, vincristine); CCV-AV (CCNU, cyclophosphamide, vincristine/Adriamycin, vincristine); CCVB (CCNU, cyclophosphamide, vincristine, bleomycin); CCVPP (CCNU, cyclophosphamide, Velban, procarbazine, prednisone); CCVV (cyclophosphamide, CCNU, VP-16, vincristine); CCVVP (cyclophosphamide, CCNU, VP-16, vincristine, Platinol); CD (cytarabine, daunorubicin); CdA (chlorodeoxyadenosine) (cladribine); 2-CdA (2-chlorodeoxyadenosine); CDC (carboplatin, doxorubicin, cyclophosphamide); CDDP, C-DDP (cis-diamminedichloroplatinum); CDDP (cisplatin); CDE (cyclophosphamide, doxorubicin, etoposide); CEAker; CEB (carboplatin, etoposide, bleomycin); CECA (cisplatin, etoposide, cyclophosphamide, Adriamycin); CeeNu (CCNU or lomustine); CEF (cyclophosphamide, epirubicin, 5-fluorouracil); celogovab (OncoScint OV103); CEM (cytosine arabinoside, etoposide, methotrexate); Centixsin; centrifugation; CEP (CCNU, etoposide, prednimustine); CEP (cyclophosphamide, etoposide, Platinol); Ceptrate SC (monoclonal antibodies); Cerubidine (daunorubicin); CEV (cyclophosphamide, etoposide, vincristine); CF (cisplatin, 5-fluorouracil); CF (citrovorum factor); CF (leucovorin); CFL (cisplatin, 5-fluorouracil, leucovorin calcium); CFM (cyclophosphamide, 5-fluorouracil, mitoxantrone); CFP (cyclophosphamide, 5-fluorouracil, prednisone); CFPT (cyclophosphamide, 5-fluorouracil, prednisone, tamoxifen); CGS 16949A; CHAD (cyclophosphamide, hexamethylmelamine, Adriamycin, DDP); CHAMOCA (Cytoxan, hydroxyurea, actinomycin D, methotrexate, Oncovin, calcium; folinate, Adriamycin); CH1VPP, Ch1VPP (chlorambucil, vinblastine, procarbazine, prednisone); CHAP (cyclophosphamide, Hexalen, Adriamycin, Platinol); CHD (cyclophosphamide, hexamethylmelamine, DDP); CHD-R (cyclophosphamide, hexamethylmelamine, DDP, radiotherapy); CHEX-UP (cyclophosphamide, hexamethylmelamine, 5-fluorouracil, Platinol); CHF (cyclophosphamide, hexamethylnelamine, 5-fluorouracil); chimeric 17-1A (C17-1A); chimeric L6 monoclonal antibodies; CHIP (cis-dichlorotranshydroxy-bis-isopropylamine platinum IV); CHIP (iproplatin); chlorambucil (CLB or Leukeran); Chlorbutin (chlorambucil); chlormethine; chlormethine HCl; 8-chlorocamp; 2-chlorodeoxyadenosine (2-CdA); chlorodeoxyadenosine; chlorotrianisene (Tace); chlorozotocin (DCNU); CHL+PRED (chlorambucil , prednisone); Ch1-VPP (chlorambucil, vinblastine, procarbazine, prednisone); CHO (cyclophosphamide, hydroxydaunomycin, Oncovin); CHOB (cyclophosphamide, hydroxydaunomycin, Oncovin, bleomycin); CHOD (cyclophosphamide, hydroxydaunomycin, Oncovin, dexamethasone); CHOP (cyclophosphamide, Halotestin, Oncovin, prednisone); CHOP (cyclophosphamide, hydroxydaunomycin, Oncovin, prednisone); CHOP-BLEO (cyclophosphamide, hydroxydaunomycin, Oncovin, prednisone, bleomycin); CHOPE (cyclophosphamide, Halotestin, Oncovin, prednisone, etoposide); CHOR (cyclophosphamide, hydroxydaunomycin, Oncovin, radiotherapy); chromic phosphate P 32; CHVP (cyclophosphamide, hydroxydaunomycin, VM-26, prednisone); CI-958, 973, 980; CIA (CCNU, ifosfamide, Adriamycin); cinchona bark; CIS 39300; cis-retinoic acid (CRA); 13-cis-retinoic acid (13-CRA); CISCA, CisCA (cisplatin, cyclophosphamide, Adriamycin); CISCAii/BViv (cisplatin, cyclophosphamide, Adriamycin, vinblastine, bleomycin); cis-DDP (cisplatin); cis-diamminedichloroplatinum (cisplatin); cisplatin (CDDP or cis-platinum or DDP or Platinol); cisplatin/collagen matrix; citrovorum factor (CF); citrovorum rescue; CIVPP (chlorambucil, vinblastine, procarbazine, prednisone); cladribine (Leustatin); clofarabine; CLB (chlorambucil); CMC (cyclophosphamide, methotrexate, CCNU); CMC-VAP (cyclophosphamide, methotrexate, CCNU, vincristine, Adriamycin,; procarbazine); CMF (cyclophosphamide, methotrexate, 5-fluorouracil); CMF-AV (cyclophosphamide methotrexate, 5-fluorouracil, Adriamycin, vincristine); CMFAVP (cyclophosphamide, methotrexate, 5-fluorouracil, Adriamycin, vincristine,; prednisone); CMF-BLEO (cyclophosphamide, methotrexate, 5-fluorouracil, bleomycin); CMF-FLU (cyclophosphamide, methotrexate, 5-fluorouracil, fluoxymesterone); CMFH (cyclophosphamide, methotrexate, 5-fluorouracil, hydroxyurea); CMFP (cyclophosphamide, methotrexate, 5-fluorouracil, prednisone); CMFPT (cyclophosphamide, methotrexate, 5-fluorouracil, prednisone, tamoxifen); CMF-PTH (cyclophosphamide, methotrexate, 5-fluorouracil, prednisone, tamoxifen,; Halotestin); CMFP-VA (cyclophosphamide, methotrexate, 5-fluorouracil, prednisone, vincristine,; Adriamycin); CMFT (cyclophosphamide, methotrexate, 5-fluorouracil, tamoxifen); CMF-TAM (cyclophosphamide, methotrexate, 5-fluorouracil, tamoxifen); CM-5-FU (cyclophosphamide, methotrexate, 5-fluorouracil); CMFV (cyclophosphamide, methotrexate, 5-fluorouracil, vincristine); CMFVAT (cyclophosphamide, methotrexate, 5-fluorouracil, vincristine, Adriamycin,; testosterone); CMFVP (cyclophosphamide, methotrexate, 5-fluorouracil, vincristine, prednisone); CMH (cyclophosphamide, m-AMSA, hydroxyurea); CMOPP, C-MOPP (cyclophosphamide, mechlorethamine, Oncovin, procarbazine,; prednisone); CMP (CCNU, methotrexate, procarbazine); CMPF (cyclophosphamide, methotrexate, prednisone, 5-fluorouracil); CMV (cisplatin, methotrexate, vinblastine); CNF (cyclophosphamide, Novantrone, 5-fluorouracil); CNOP, C-NOP (cyclophosphamide, Novantrone, Oncovin, prednisone); COAP (cyclophosphamide, Oncovin, ara-C, prednisone); COAP-BLEO (cyclophosphamide, Oncovin, ara-C, prednisone, bleomycin); COB (cisplatin, Oncovin, bleomycin); COB-MAM (cyclophosphamide, Oncovin, bleomycin, methotrexate, Adriamycin,; MeCCNU); COF/COM (cyclophosphamide, Oncovin, 5-fluorouracil/ cyclophosphamide, Oncovin,; methotrexate); colaspase; COM (cyclophosphamide, Oncovin, methotrexate); COM (cyclophosphamide, Oncovin, MeCCNU); COMA-A (cyclophosphamide, Oncovin, methotrexate, Adriamycin, ara-C); COMB (cyclophosphamide, Oncovin, methotrexate, bleomycin); COMB (cyclophosphamide, Oncovin, MeCCNU, bleomycin); COMBAP (cyclophosphamide, Oncovin, methotrexate, bleomycin, Adriamycin,; prednisone); COMe (cyclophosphamide, Oncovin, methotrexate); COMET-A (cyclophosphamide, Oncovin, methotrexate, leucovorin, etoposide, ara-c); COMF (cyclophosphamide, Oncovin, methotrexate, 5-fluorouracil); COMLA (cyclophosphamide, Oncovin, methotrexate, leucovorin, ara-C); COMP (Cyclophosphamide, Oncovin, methotrexate, prednisone); conjugated estrogens; CONPADRI, COPADRI-I (cyclophosphamide, Oncovin, L-phenylalanine mustard,; Adriamycin); Consensus interferon; Cooper CMFVP (cyclophosphamide, methotrexate, 5-fluorouracil, vincristine, prednisone); Cooper Regimen (cyclophosphamide, methotrexate, 5-fluorouracil, vincristine, prednisone); COP (cyclophosphamide, Oncovin, prednisone); COP (cyclophosphamide, Oncovin, prednisolone); COPA (cyclophosphamide, Oncovin, prednisone, Adriamycin); COPA-BLEO (cyclophosphamide, Oncovin, prednisone, Adriamycin, bleomycin); COPAC (CCNU, Oncovin, prednisone, Adriamycin, cyclophosphamide); COP-B, COPB (cyclophosphamide, Oncovin, prednisone, bleomycin); COP-BLAM (cyclophosphamide, Oncovin, prednisone, bleomycin, Adriamycin, Matulane); COP-BLEO (cyclophosphamide, Oncovin, prednisone, bleomycin); COPE (cyclophosphamide, Oncovin, Platinol, etoposide); COPP (CCNU, Oncovin, procarbazine, prednisone); COPP (cyclophosphamide, Oncovin, procarbazine, prednisone); Cosmegen (dactinomycin); CP (Cytoxan, Platinol); CP (cyclophosphamide, prednisone); CPA (cyclophosphamide); CPB (cyclophosphamide, Platinol, BCNU); CPC (cyclophosphamide, Platinol, carboplatin); CPDD (cis-platinum diamminedichloride); CPM (CCNU, procarbazine, methotrexate); CPOB (cyclophosphamide, prednisone, Oncovin, bleomycin); CPT-11 (camptothecin-11); CPTR (cyproterone); CRA (cis-retinoic acid); 13-CRA (13-cis-retinoic acid); Crasnitin (C-asparaginase); CRF-187; crisnatol mesylate; CROP (cyclophosphamide, rubidazone, Oncovin, prednisone); CROPAM (cyclophosphamide, rubidazone, Oncovin, prednisone, L-asparaginase,; methotrexate); CT (cytarabine, thioguanine); CTCb (cyclophosphamide, thiotepa, carboplatin); CTX (cyclophosphamide); CTX-Plat (cyclophosphamide, Platinol); CV 205-502; CV (cisplatin, VP-16); CVA (cyclophosphamide, vincristine, Adriamycin); CVA-BMP (cyclophosphamide, vincristine, Adriamycin, BCNU, methotrexate,; procarbazine); C-VAD, CVAD (cyclophosphanide, vincristine, Adriamycin, dexamethasone); CVB (CCNU, vinblastine, bleomycin); CVBD (CCNU, vinblastine, bleomycin, dexamethasone); CVD (cisplatin, vinblastine, dacarbazine); CVEB (cisplatin, Velban, etoposide, bleomycin); CVI (carboplatin, VePesid, ifosfamide, Mesnex uroprotection); CVM (cyclophosphamide, vincristine, methotrexate); CVP (cyclophosphamide, vincristine, prednisone); CVP-BLEO (cyclophosphamide, vincristine, prednisone, bleomycin); CVPP (CCNU, vinblastine, prednisone, procarbazine); CVPP (cyclophosphamide, vinblastine, procarbazine, prednisone); CVPP-CCNU (cyclophosphamide, vinblastine, procarbazine, prednisone, CCNU); CY (cyclophosphamide or Cytoxan); CyADIC (cyclophosphamide, Adriamycin, DTIC); CYC (cyclophosphamide); cyclocreatine; cyclohexylnitrosourea (CCNU); cyclophosphamide (CPA or CPM or CYC); Cycoblastin (cyclophosphamide); CyHOP (cyclophosphamide, Halotestin, Oncovin, prednisone); cyproterone (CPTR); cysteamine dichloroplatinum-2; CYT-103-Y-90 (OncoRad); CytaBOM, CYTABOM (cytarabine, bleomycin, Oncovin, mechlorethamine); Cytadren (aninoglutethimide); cytarabine (ara-C or Cytosar-U or cytosine arabinoside); Cytosar-U (cytarabine); cytosine arabinoside (ara-C); Cytoxan (CTX); Cytoxan Lyophilized; CyVADACT, CY-VA-DACT (cyclophosphamide, vincristine, Adriamycin, dactinomycin); CyVADIC (cyclophosphamide, vincristine, methotrexate, Adriamycin, DTIC); CyVMAD (cyclophosphamide, vincristine, methotrexate, Adriamycin, DTIC); DA (daunorubicin, ara-C); dacarbazine (DTIC); DACT (dactinomycin); dactinomycin (actinomycin D); DAP (dianhydrogalactitol, Adriamycin, Platinol); DAP/TMP (dapsone, trimethoprim); DAT (daunomycin, ara-C, 6-thioguanine); DATVP (daunomycin, ara-C, 6-thioguanine, vincristine, prednisone); Datelliptium (ellipticine); daunomycin (DNM); daunorubicin hydrochloride (Cerubidine or DNR); DaunoXome (liposomal daunorubicin); DAV (dibromodulcitol, Adriamycin, vincristine); DAVA (desacetyl vinblastine amide); DAVH (dibromodulcitol, Adriamycin, vincristine, Halotestin); DBD (dibromodulcitol); DBV (dacarbazine, BCNU, vincristine); DC (daunorubicin, cytarabine); DCCMP (daunorubicin, cyclocytidine, 6-metacaptopurine, prednisone); DCF (2-deoxycoformycin or pentostatin); DCM (dichloromethotrexate); DCMP (daunorubicin, cytarabine, 6-metacaptopurine, prednisone); DCT (daunorubicin, cytarabine, thioguanine); DCV (dacarbazine, CCNU, vincristine); DDP (cis-diaminodichloroplatinum or cisplatin); 3-deazaguanine; DECAL (dexamethasone, etoposide, cisplatin, ara-C, L-asparaginase); Decapeptyl (triptorelin); decitabine; deferoxamine; Deladiol-40 (estradiol); Delatest (testosterone); Delatestryl (testosterone); Delestrogen (estradiol); 2-deoxy-5-azacitidine (DAC); deoxycoformycin (DCF or pentostatin); deoxyspergualin (DSG), depAndro, depAndro 200 (testosterone); Depofoam encapsulated cytarabine (DTC 101); Depo-Provera; Depotest (testosterone); Depo-Testosterone; dexormaplatin; dexverapamil; dezaguanine; dezaguanine mesylate; DFDC (gemcitabine); DFMO (eflornithine); DFMO-MGBG; DFV (DDP, 5-fluorouracil, VePesid); DHAC (azacitidine); DHAD (mitoxantrone);

DHAP (dexamethasone, high-dose ara-C, Platinol); DI 694; diaziquone (aziridinylbenzoquinone); dibromodulcitol (Mitolactol); Dicorvin; didemnin B; didox; diethyldithiocarbarate (DTC); diethylstilbestrol diphosphate; dihematoporphyrin ethers; dihydro-5-azacitidine (azacitidine or DHAC); DIMOPP (dose-intensified MOPP); Dioval XX, Dioval 40 (estradiol); DL (doxorubicin, lomustine); DM (dexamethasone); DMC (dactinomycin, methotrexate, cyclophosphamide); DMP 840; DNM (daunomycin); DNR (daunorubicin); DOAP (daunorubicin, Oncovin, ara-C, prednisone); docetaxel; dolasestron; DOX (doxorubicin); Doxil (liposome formulation of doxorubicin); doxorubicin (Adriamycin or DOX); Drolban; droloxifene; dromostanolone propionate (Drostanolone); dronabinol; Drostanolone; DTC (diethyldithiocarbamate); DTIC (dacarbazine); DTIC-ACTD (DTIC, actinomycin D); DTIC-Dome (dacarbazine); duazomycin; Durabolin (nandrolone phenpropionate); Duragen (estradiol); Duralutin (hydroxyprogesterone); Duratest (testosterone); Durathate (testosterone); DVB (DDP, vindesine, bleomycin); DVP (daunorubicin, vincristine, prednisone); DVPL-ASP (daunorubicin, vincristine, prednisone, L-asparaginase); DZAPO (daunorubicin, azacitidine, ara-C, prednisone, Oncovin); EAP (etoposide, Adriamycin, Platinol); Eastern Cooperative Oncology Group (ECOG); EBAP (Eldisine, BCNU, Adriamycin, prednisone); echinomycin; EBRT (external beam radiation therapy); ECHO (etoposide, cyclophosphamide, hydroxydaunomycin, Oncovin); 10-EDAM (10-ethyl-10-deaza-aminopterin) (Edatrexate); ECMV (etoposide, Cytoxan, methotrexate, vincristine); ECOG (Eastern Cooperative Oncology Group); EDAM (10-ethyl-deaza-aminopterin or 10-EdAM); EDAP (etoposide, dexamethasone, ara-C, Platinol); Edatrexate (10-EDAM) (10-ethyl-10-deaza-aminopterin); eflornithine (DFMO); Efudex (fluorouracil); EFP (etoposide, fluorouracil, Platinol); Einhorn regimen; Eldisine (vindesine sulfate); ELF (etoposide, leucovorin, 5-fluorouracil); Elipten (aminoglutethimide); Elliott's B solution; ellipticine; elsamitrucin; Elspar (asparaginase); EMACO (etoposide, methotrexate, actinomycin D, cyclophosphamide, Oncovin); Emcyt (estramustine); E-MVAC (escalated methotrexate, vinblastine, Adriamycin, cyclophosphamide); Endoxan-Asta (cyclophosphamide); enloplatin; enpromate; EP (etoposide, Platinol); EPI (epirubicin); epi-ADR (epinephrine-Adriamycin); epipropidine; epirubicin; epirubicin HCl; EPO (erythropoietin); EPOCH (etoposide, prednisone, Oncovin, cyclophosphamide, Halotestin); Epodyl; Epogen; Eprex (erythropoietin); erbulozole; Ergamisol (levamisole); Erwinase; erwinia asparaginase; erwinia L-asparaginase; ESHAP (etoposide, Solu-Medrol, ara-C, Platinol); esorubicin; esorubicin HCl; esperamycin; Esterified estrogens; Estinyl; Estra-L (estradiol); Estrace; estradiol; Estradurin; estramustine (Emcyt); Estratab; Estraval; Estrone 5; etanidazole; ethacrynic acid; ethinyl estradiol; Ethiodol; Ethiofos (WR2721); 10-ethyl-10-deaza-aminopterin (10-EDAM) (Edatrexate); Ethyol (amifostine); etoposide (VP-16, VePesid); etoposide phosphate; etoprine; Eulexin; EVA (etoposide, vinblastine, Adriamycin); EVAP; Everone; EVMAC (escalated methotrexate, vinblastine, Adriamycin, cisplatin); FAC (5-fluorouracil, Adriamycin, cyclophosphamide); FAC-BCG (Ftorafur, Adriamycin, cyclophosphamide, BCG); FAC-LEV (5-fluorouracil, Adriamycin, cyclophosphamide, levamisole); FAC-M (5-fluorouracil, Adriamycin, cyclophosphamide, methotrexate); FACP (Ftorafur, Adriamycin, cyclophosphamide, Platinol); FACS (5-fluorouracil, Adriamycin, cyclophosphamide, streptozocin); FACVP (5-fluorouracil, Adriamycin, cyclophosphamide, VP-16); fadrozole; fadrozole HCl (Arensin); FAM (5-fluorouracil, Adriamycin, mitomycin-C); FAM-C (5-fluorouracil, Adriamycin, methyl-CCNU); FAM-CF (5-fluorouracil, Adriamycin, mitomycin, citrovorum factor); FAME, FAMe (5-fluorouracil, Adriamycin, MeCCNU); FAMMe (5-fluorouracil, Adriamycin, mitomycin-C, MeCCNU); FAMP (fludarabine monophosphate); FAM-S (5-fluorouracil, Adriamycin, mitomycin-C, streptozocin); FAMTX (5-fluorouracil, Adriamycin, high-dose methotrexate); FAP (5-fluorouracil, Adriamycin, Platinol); Farmorubicin (epirubicin HCl); fazarabine (ara-AC); FCAP (5-fluorouracil, cyclophosphamide, Adriamycin, Platinol); FCE (5-fluorouracil, epirubicin, cyclophosphamide); F-CL (5-fluorouracil, leucovorin calciumn); FCP (5-fluorouracil, cyclophosphamide, prednisone); FEC (5-fluorouracil, epirubicin, cyclophosphamide); FED (5-fluorouracil, etoposide, DDP); Feminone (discontinued in 1993) (ethyl estradiol); fenretinide (4-HPR); filgrastim (Neupogen) (G-CSF); FIMe (5-fluorouracil, ICRF-159, MeCCNU); finasteride (MK-906); 5+2 protocol (cytarabine, daunorubicin); FK 506; FL (flutamide, leuprolide acetate); FL (flutamide, Lupron depot); FLAC (5-fluorouracil, leucovorin calcium, Adriamycin, cyclophosphamide); FLAG-Ida; FLAP (5-fluorouracil, leucovorin, Adriamycin, Platinol); FLe (5-fluorouracil, levamisole); floxuridine (FUdR); flucytosine (Ancobon or 5-FC); Fludara (fludarabine); fludarabine (FAMP or Fludara); fludarabine phosphate; fluorodeoxyuridine (FUdR); Fluoroplex cream, topical (fluorouracil); fluorouracil (Adrucil or Efudex or 5-fluorouracil or 5-FU or Fluoroplex); Fluosol/BCNU (Fluosol-DA20, BCNU); fluoxymesterone (FMX or Halotestin); fluorodeoxyuridine (FUDR); Fluoroplex (5-fluorouracil); flurocitabine; flutamide (Eulexin or FLUT); FMS (5-fluorouracil, mitomycin-C, streptozocin); FMV (5-fluorouracil, methyl CCNU, vincristine); FNM (5-fluorouracil, Novantrone, methotrexate); FOAM (5-fluorouracil, Oncovin, Adriamycin, mitomycin-C); Folex (methotrexate) (discontinued in 1992); Folex PFS (methotrexate); folinic acid (leucovorin); FOM (5-fluorouracil, Oncovin, mitomycin-C); FOMi (5-fluorouracil, Oncovin, mitomycin-C); Fosfestrol (diethylstilbestrol diphosphate); fosquidone; fostriecin; fostriecin sodium; fotemustine (S 10036); FRACON (framycetin, colistin, nystatin); Ftorafur (1,2-tetrahydrofuranyl-5-fluorouracil); 5-FU (5-fluorouracil); FUDR (floxuridine); FUdR (5-fluorouracil deoxyribonucleoside); FUM (5-fluorouracil, methotrexate); Fungizone (amphotericin-B); FUra (fluorouracil); FURAM (Ftorafur, Adriamycin, mitomycin-C); Furhman nuclear grade; FUVAC (5-fluorouracil, vinblastine, Adriamycin, cyclophosphamide); FXM (fluoxymesterone or Halotestin); FZ (flutamide, Zoladex); galamustine (G-6-M); gallium nitrate (GAN); Gamimune Normal (immune globulin); gemcitabine (DFDC) (Gemzar); gemcitabine HCl; Gemzar (gemcitabine); Gesterol (progesterone); GL331; Gliadel; glycyrrhetinic acid; GM-CFU (granulocyte-macrophage colony-forming unit); GM-CSF (granulocyte-macrophage colony-stimulating factor); GOD-26MM; gold Au 198; goserelin acetate (ZDX or Zoladex); GVAX; Gynogen L.A. "10", Gynogen L.A. "20", Gynogen L.A. "40" (estradiol); H-447; H (Halotestin); HAD (hexamethylenamine, Adriamycin, DDP); Halodrin; Halotestin; HAM (hexamethylenamine, Adriamycin, melphalan); HAM (hexamethylenamine, Adriamycin, methotrexate); HAMP (hexamethylenamine, Adriamycin, methotrexate, Platinol); HC (hydrocortisone); HCAO (hexamethylenamine, cyclophosphamide, Adriamycin, Platinol); H-CAP (hexamethylenamine, cyclophosphamide, Adriamycin, Platinol); 4-HC (4-hydroperoxycyclophosphamide or Pergamid); HDARA-C (high-dose ara-C); HDC (pentostatin); HDMTX (high-dose methotrexate); HDMTX-CF (high-dose methotrexate, citrovorum factor); HDMTX/LV (high-dose methotrexate, leucovorin); HDPEB (high-dose PEB or Platinol, etoposide, bleomycin); HD-VAC (high-dose methotrexate plus vinblastine, Adriamycin, cisplatin); hepsulfam; HER2 (monoclonal antibody); Hexa-CAF (Hexalen, cyclophosphamide, Adrucil, Folex); Hexalen (altretamine); hexamethylene; hexamethylene bisacetamide; hexamethylmelamine; Hexastat (altretamine); HiC-COM (ara-C, citrovorum factor, allopurinol, Elliot B solution, cyclophosphamide,; Oncovin, methotrexate); HIDAC, HiDAC (high-dose ara-C); high-risk ATAC (L-asparaginase, ara-C, VP-16, anti-J2 26 monoclonal antibody,; anti-CALLA hybridoma antibody); Histerone; HMBA (hexamethylene bisacetamide); HMM (Hexalen); HMTX (high-dose methotrexate); HN2 (nitrogen mustard); HOAP-BLEO (hydroxydaunomycin, Oncovin, ara-C, prednisone, bleomycin); homoharringtonine; HOP (hydroxydaunomycin, Oncovin, prednisone); HPR (fenretinide); 4-HPR (fenretinide); HU (hydroxyurea); human IgM monoclonal antibody to cytomegalovirus; HXM (hexamethylmelamine); Hybolin Improved (nandrolone phenpropionate); Hybri-CEAker; Hy-Gestrone; hydrazine sulfate; 4-hydroxyperoxycyclophosphamide; Hydrea (hydroxyurea); 4-hydroperoxycyclophosphamide (4-HC); hydroxycarbamide; hydroxyurea (Hydrea); Hylutin; Hyprogest; Hyproval; Hyproxon; ICE (ifosfamide, carboplatin, etoposide); ICI D1694 (Tomudex); ICRF-187; IDA (idarubicin); Idamycin (idarubicin HCl); idarubicin; idarubicin HCl; IDEC-C2B8; IDMTX (intermediate-dose methotrexate); IDX (4'-iodo-4'deoxydoxorubicin); Ifex (ifosfamide); IFF (ifosfamide); IFLrA (recombinant interferon alpha); IFM (ifosfamide); IFN-A (interferon alpha); IFN-alpha 2a (interferon alpha 2a); IFN-G (gamma interferon); IFOS (ifosfamide); ifosfamide; IFX (ifosfamide); IL-2 (interleukin-2); ilmofosine; IMF (Ifex, mesna, Folex, 5-fluorouracil); imidazole carboxamide (dacarbazine); ImmTher; ImmuRAID-AFP; ImmuRAID-CEA; ImmuRAID-hCG; ImmuRAID-LL2; ImmuRAIT-LL2; Imuran (azathioprine); Imuvert (*Serratia marcescens* extract); IMVP-16 (ifosfamide, methotrexate, VP-16); interferon alfa; interferon alfa-2a; interferon alfa-2b; interferon beta (Serono, R-Frone); interferon gamma-1b; interleukin-1, 1a, 2,3, 4, 6, 11; intoplicine; Intron-A; iododeoxyuridine; isotretinoin; iododeoxyuridine; IPP (isopropyl pyrrolizine); iproplatin; iridium; irinotecan; Isorvorin (L-leucovorin); IT MTX (intrathecal methotrexate); IUdR (idoxuridine); JT1001; Kestrone 5; KGC (Keflin, gentamicin, carbenicillin); Kynacyte; ladakamycin; L.A.E.20 (discontinued in 1992); LAM (L-asparaginase, methotrexate); lanreotide acetate; LAPOCA (L-asparaginase, prednisone, Oncovin, cytarabine, Adriamycin); L-ASP (L-asparaginase); L-asparaginase; L-buthionine sulfoximine; L-CF (leucovorin-citrovorum factor); LCR (vincristine); LDI-200; letrozole; Leucomax (molgramostim); L-leucovorin; leucovorin calcium; Leukeran (chlorambucil); Leukine (sargramostim); Leukoglobulin; leuprolide acetate (Leuprorelin); Leuprorelin; leurocristine; Leustatin (2-CdA or cladribine); LEV (levamisole hydrochloride); levamisole (Ergamisol); LGD-1069; liarozole fumarate; liarozole HCl; linker protocol; Linomide (roquinimex); Lipidox (liposomal doxorubicin); liposomal doxorubicin (TLC D-99); liposomal MTP-PE; liposomal nystatin; L-leucovorin (Isovorin); LMP (Leukeran, methotrexate, 5-fluorouracil); L-PAM (L-phenylaline mustard or melphalan); lobaplatin; LOMAC (leucovorin, Oncovin, methotrexate, Adriamycin, cyclophosphamide); lometrexol; lomustine (CCNU); lonidamine; losoxantrone; losoxantrone HCl; LP 2307; L-PAM (L-phenylalanine mustard) (melphalan); Lupron; Lupron Depot; LuVax (monoclonal antibodies); LV (leucovorin); L-VAM (Lupron, Velban, Adriamycin, Mutamycin); LVVP (Leukeran, vinblastine, vincristine, prednisone); Lysodren; M2 (vincristine, carmustine, cyclophosphanide, melphalan, prednisone); MAb, MAB (monoclonal antibody); MAb B72,3; MAb-L6; MABOP (Mustargen, Adriamycin, bleomycin, Oncovin, prednisone); MAC (methotrexate, actinomycin D, cyclophosphamide); MAC (methotrexate, Adriamycin, cyclophosphamide); MAC (mitomycin-C, Adriamycin, cyclophosphamide); MACC (methotrexate, Adriamycin, cyclophosphamide, CCNU); MACHO (methotrexate, asparaginase, cyclophosphamide, hydroxydaunomycin, Oncovin); MACOP-B (methotrexate, Adriamycin, cyclophosphamide, Oncovin, prednisone,; bleomycin); Macrolin (macrophage colony-stimulating factor); Macstim (macrophage colony-stimulating factor); MAD (MeCCNU, Adriamycin); MADDOC (mechlorethamine, Adriamycin, dacarbazine, DDP, Oncovin,; cyclophosphamide); MAID (mesna, Adriamycin, interleukin-3, dacarbazine); MAID (Mesnex, Adriamycin, Ifex, dacarbazine); maitansine; MAK 195 F (monoclonal antibodies); m-AMSA (amsacrine); MAP (melphalan, Adriamycin, prednisone); MAP (mitomycin-C, Adriamycin, Platinol); masoprocol; MAT (multiple agent therapy); Matulane (procarbazine); maytansine; MAZE (m-AMSA, azacitidine, etoposide); M-BACOD (high-dose methotrexate, bleomycin, Adriamycin, cyclophosphamide, Oncovin,; dexamethasone); M-BACOS (methotrexate, bleomycin, Adriamycin, cyclophosphamide, Oncovin,; Solu-Medrol); M-BAM (cyclophosphamide, total body irradiation, monoclonal antibodies); MBC (methotrexate, bleomycin, cisplatin); MBD (methotrexate, bleomycin, cisplatin); MC (mitoxantrone, cytarabine); MCBP (melphalan, cyclophosphamide, BCNU, prednisone); MCP (melphalan, cyclophosphamide, prednisone); M-CSF (macrophage colony-stimulating factor); MCV (methotrexate, cisplatin, vinblastine); MD 28314QA; MDAM; MDL18, 962; MDL 73,147EF; MDLO (metoclopramide, dexamethasone, lorazepam, ondansetron); MDX210 (humanized anti-cancer bispecific antibody); MeCCNU (methyl-CCNU or semustine); mechlorethamine; MECY (methotrexate, cyclophosphamide); medroxyprogesterone; MeFA (methyl-CCNU, 5-fluorouracil, Adriamycin); Megace (megestrol acetate); megestrol acetate (Megace); Melacine (melanoma vaccine); melanoma vaccine (Melacine); melanoma cell lysate vaccine; melengestrol acetate; MeliBu (busulfan); Melimmune-1 (monoclonal antibodies); Melimmnune-2 (monoclonal antibodies); melphalan; melphalan IV; MelVax (monoclonal antibodies); Memorial Sloan-Kettering protocol; Menest (esterified estrogens); menogaril; MePRDL (methylprednisolone); merbarone; mercaptopurine; 6-mercaptopurine (6-MP or Purinethol); mesna (Mesnex); Mesnex (mesna); methionyl granulocyte CSF, recombinant; methionyl human granulocyte CSF, recombinant; Methosarb; methotrexate (MTX); methotrexate LFP sodium; methotrexate sodium; methotrexate/Azone (methotrexate, laurocapram); methyl-CCNU (semustine or MeCCNU); methylmercaptopurine; Methylprednisolone; Meticorten; metoprine; Mexate; MF (methotrexate, 5-fluorouracil); MF (mitomycin, 5-fluorouracil); MFP (melphalan, 5-fluorouracil, Provera); MGDF (megakaryocyte growth and development factor); MICE (mesna rescue, ifosfamide, carboplatin, etoposide); MIFA (mitomycin, fluorouracil, Adriamycin); mifepristone (RU486); MIH (procarbazine); M (mesna, ifosfamide, Novantrone, etoposide); MINE/ESHAP; mini-COAP (cyclophosphamide, Oncovin, ara-C, prednisone); MINT; MIP-1 alpha; misonidazole; Mithracin (plicamycin); mithramycin (now plicamycin); mitindomide; MITO (mitomycin-C); mitocarcin; mitocromin; mitogillin; mitoguazone; mitolactol (dibromodulcitol); mitomalcin; mitomycin; mitomycin-C (MMC or Mutamycin); mitosper; mitotane; mitoxantrone (Novantrone); MM (mercaptopurine, methotrexate); MMC (mitomycin-C); MMOPP (methotrexate, mechlorethamine, Oncovin, procarbazine, prednisone); MMPR (methylmercaptopurine); MMPT (methylprednisolone pulse therapy); MNA (N-monomethyl-L-arginine); MOAB, MoAb, MAB (monoclonal antibody); MOAD (methotrexate, Oncovin, L-asparaginase, dexamethasone); MOAP (PEG-asparaginase, Oncovin, methotrexate, prednisone); MOB (Mustargen, Oncovin, bleomycin); MOB-III (mitomycin-C, Oncovin, bleomycin, cisplatin); MOCA (methotrexate, Oncovin, cyclophosphamide, Adriamycin); Modrastane; MOF (MeCCNU, Oncovin, 5-fluorouracil); MOF (methotrexate, Oncovin, 5-fluorouracil); MOF-STREP (MeCCNU, Oncovin, 5-fluorouracil); molgramostim; MOMP (mechlorethamine, Oncovin, methotrexate, prednisone); monoclonal antibodies; monoclonal antibodies recognizing B-cell lymphoma idiotypes; monoclonal antibody 17-1A; monoclonal antibody PM-81; monoclonal antibody PM-81 & AML-2-23; Monogen; monomercaptoundecahydro-closo-DQ decaborate sodium; Monox-IX; MOP (mechlorethamine, Oncovin, prednisone); MOP (mechlorethamine, Oncovin, procarbazine); MOP (melphalan, Oncovin, methylprednisolone); MOP-BAP (mechlorethamine, Oncovin, procarbazine, bleomycin, Adriamycin, prednisone); MOPP (mechlorethamine, Oncovin, procarbazine, prednisone); MOPP (methotrexate, Oncovin, procarbazine, prednisone); MOPP-ABV (mechlorethamine, Oncovin, procarbazine, prednisone, Adriamycin,; bleomycin, vinblastine); MOPP-ABVD (mechlorethamine, Oncovin, procarbazine, prednisone, Adriamycin,; bleomycin, vinblastine, dacarbazine); MOPP-LO BLEO (mechlorethamine, Oncovin, procarbazine, prednisone, bleomycin); MOPPHDB (mechlorethamine, Oncovin, procarbazine, prednisone, high-dose bleomycin); MOP-PLDB (mechlorethamine, Oncovin, procarbazine, prednisone, low-dose bleomycin); MOPr (mechlorethamine, Oncovin, procarbazine); MP (melphalan, prednisone); 6-MP (6-mercaptopurine); MPFL (methotrexate, Platinol, 5-fluorouracil, leucovorin, calcium); MPL (melphalan); MPL+PRED (melphalan, prednisone); MTX (methotrexate); MTX+MP (methotrexate, mercaptopurine); MTX+MP+CTX (methotrexate, mercaptopurine, Cytoxan); Murine L6 monoclonal antibody; Mustargen (mechlorethamine HCl); mustine HCl; Mutamycin (mitomycin); MV (mitoxantrone, VP-16); MVAC (methotrexate, vinblastine, Adriamycin, cisplatin); MVF (mitoxantrone, vincristine, 5-fluorouracil); MVP (mitomycin-C, vinblastine, Platinol); MVPP (mechlorethamine, vinblastine, procarbazine, prednisone); MVT (mitoxantrone, VP-16, thiotepa); MVVPP (mechlorethamine, vincristine, vinblastine, procarbazine, prednisone); Myleran; Mylosar (5-azacytidine); N-901-blocked ricin (Oncolysin S); NAC (nitrogen mustard, Adriamycin, CCNU); Nadrobolic (discontinued in 1994); nafidimide (amonafide); Navelbine (vinorelbine); neon particle; Neosar (cyclophosphamide); neptamustine; NEU differentiation factor; Neupogen (filgrastim); Neu-Sensamide; N-methylhydrazine; nimustine; Nipent (pentostatin); nitrogen mustard; NM (mechlorethamine); N-methylhydrazine (procarbazine); N-monomethyl-L-arginine (MNA); nocodazole; nogalamycin; Nolvadex (tamoxifen); Novantrone (mitoxantrone); NovoSeven; Numega (interleukin-11); OAP (Oncovin, ara-C, prednisone); OAP-BLEO (Oncovin, ara-C, prednisone, bleomycin); OctreoScan 111 (Indium In 111 pentetreotide); octreotide (Sandostatin); O-DAP (Oncovin, dianhydrogalactitol, Adriamycin, Platinol); OLX-102; OMAD (Oncovin, methotrexate, Adriamycin, dactinomycin); onapristone; Oncaspar (pegaspargase); Oncoject; Oncol; Oncolym; Oncolysin B, Oncolysin S; Onco Non-Small Cell; OncoPurge; OncoRad OV103 (CYT-103-Y-90); OncoRad Bladder; OncoRad Ovarian; OncoRad Prostate; OncoScint CR/OV; OncoScint OV103 (celogobab); OncoScint PR; OncoTrac; Oncovin (vincristine); Oncozole (3-deazaguanine); ondansetron; OPAL (Oncovin, prednisone, L-asparaginase); OPEN (Oncovin, prednisone, etoposide, Novantrone); OPP (Oncovin, procarbazine, prednisone); OPPA (Oncovin, procarbazine, prednisone, Adriamycin); Ora-Testryl; ormaplatin; omithine; Orthozyme-CD5; Ossirene; ovarian rhenium-186 MAb; oxisuran; P32; PAB-Esc-C (Platinol, Adriamycin, bleomycin, escalating doses of cyclophosphamide); PAC (Platinol, Adriamycin, cyclophosphamide); PACE (Platinol, Adriamycin, cyclophosphamide, etoposide); paclitaxel (Taxol); PALA (N-phosphonoacetyl-L-aspartate); PAM, L-PAM (phenylalanine mustard); Panel Quest; Panorex (monoclonal antibody 17-1A); Paraplatin (carboplatin); PATCO (prednisone, ara-C, thioguanine, cyclophosphamide, Oncovin); PAVe (procarbazine, Alkeran, Velban); PBV (Platinol, bleomycin, vinblastine); PCB (procarbazine); PCE (Platinol, cyclophosphamide, Eldisine); PCNU; PCV (procarbazine, CCNU, vincristine); PEB (Platinol, etoposide, bleomycin); PEC (Platinol, etoposide, cyclophosphamide); PEG-ADA (Adagen, pegademase bovine); PEG-ASP (PEG-asparaginase); PEG-L-asparaginase; pegaspargase; peliomycin; Penclomedine; pentamustine; pentostatin; PEP (Procytox, epipodophyllotoxin-derivative, prednisolone); peplomycin; perfosfamide; Pergamid; PF+E (Platinol, 5-fluorouracil plus etoposide, methotrexate, leucovorin); PFL (Platinum, 5-fluorouracil, leucovorin calcium); PFM (Platinol, 5-fluorouracil, methotrexate); PFT (phenylalanine mustard, 5-fluorouracil, tamoxifen); phenylalanine mustard; phenylbutyrate; Phosphocol P32; Photofrin; PHRT (procarbazine, hydroxyurea, radiotherapy); PIA (Platinol, ifosfamide, Adriamycin); pipobroman; piposulfan; pirarubicin; pirazofurin; piritrexim; piroxantrone; PIXY; PIXY 321; Pixykine; Platinol (cisplatin); Platinol-AQ; platinum diamminodichloride; plicamycin; plomestane; PM (prednimustine); PMB (Platinol, methotrexate, bleomycin); PMF (phenylalanine mustard, methotrexate, 5-fluorouracil); PMFAC (prednisone, methotrexate, 5-fluorouracil, Adriamycin, cyclophosphamide); P-MVAC (Platinol, methotrexate, vinblastine, Adriamycin, carboplatin); POC (procarbazine, Oncovin, CCNU); POCA (prednisone, Oncovin, cytarabine, Adriamycin); POCC (procarbazine, Oncovin, cyclophosphamide, CCNU); POG protocol (Pediatric Oncology Group); polyestradiol; POMP (prednisone, Oncovin, methotrexate, Purinethol); porfimer sodium; porfiromycin; porton asparaginase; PPI-002; PRDL (prednisolone); PRED (prednisone); prednimustine; PRH-E (Platinol, etanidazole); PRIME (procarbazine, ifosfamide, methotrexate); Pro-Depo; procarbazine; Procrit; Progens; Progynon pellets; Prokine (sargramostim); Proleukin (aldesleukin); Proloid (discontinued in 1992); ProMACE (prednisone, methotrexate, Adriamycin, cyclophosphamide, etoposide); ProMACE-CytaBOM (prednisone, methotrexate, Adriamycin, cyclophosphamide,; etoposide, cytarabine, bleomycin, Oncovin, methotrexate); ProMACE-MOPP (procarbazine, methotrexate, Adriamycin, cyclophosphamide, etoposide,; Mustargen, Oncovin, procarbazine, prednisone); properomine protocol; Proscar; pulse VAC (vincristine, actinomycin D, cyclophosphamide); Purinethol (mercaptopurine); puromycin; PUVA (psoralens, ultraviolet A); PVA (prednisone, vincristine, asparaginase); PVB (Platinol, vinblastine, bleomycin); PVDA (prednisone, vincristine, daunorubicin, asparaginase); PVP (Platinol, VP-16); pyrazine diazohydroxide; pyrazoloacridine; pyridoglutethimide (Rogletimide); Quadramet; R-837; Radinyl (etanidazole); Ralox; recombinant interleukin-2; Recombinate; Renova (tretinoin emollient cream); Retin-A; retinoic acid; R-Frone (interferon beta, Serono); Rheumatrex (methotrexate sodium); RIDD (recombinant interleukin-2, dacarbazine, DDP); rIFN-A; rIFN-gamma; RIGS/ACT (adoptive cellular therapy); riboprine; ricin (blocked) conjugated murine monoclonal antibody; RIDD (recombinant interleukin-2, dacarbazine, DDP); RMP-7; ROAP (rubidazone, Oncovin, ara-C, prednisone); Roferon-A; Rogletimide (pyridoglutethimide); Rubrex (doxorubicin); rufocromomycin; St. Jude Research Children's Hospital protocol; Salagen; SAM (streptozocin, Adriamycin, methyl-CCNU); Sandimmune (cyclosporine); Sandostatin (octreotide); sargramostim (Prokine); SCAB (streptozocin, CCNU, Adriamycin, bleomycin); semustine (methyl-CCNU); Serono (interferon beta, R-Frone); *Serratia marcescens* extract; 7+3 protocol (cytarabine, daunorubicin); 7U85; Sialyl Tn-KLH; SIMAL-pilot (ara-C, hydrocortisone, mesna, prednisone, VP-16, leucovorin); SIMAL-second induction/maintenance (prednisone, L-asparaginase, daunomycin, VM-26,; methotrexate, ara-C, VP-16, leucovorin); SIMAL-bone marrow transplant (ara-C, methotrexate, prednisone); Simon capsule (cervical); simtrazene; single-chain antigen-binding proteins; SK (Sloan-Kettering protocol; SMF (streptozocin, mitomycin-C, 5-fluorouracil); sparfosic acid; sparsomycin; Specifid (discontinued in 1994); Spherex; spirogermanium; spiromustine; spiroplatin; S-P-T "liquid" capsules; SR-2508; SSTN (octreotide or Sandostatin); ST1-RTA immunotoxin; STAMP protocol (Solid Tumor Autologous Bone Marrow Program); STEAM (streptonigrin, thioguanine, cyclophosphamide, actinomycin, mitomycin); STEPA (thiotepa); Sterecyt; Stilphostrol; streptonigrin; streptozocin; streptozotocin; SU101; sulofenur; super-CM regimen (cyclophosphamide, methotrexate, 5-fluorouracil); Suprefact (buserelin); suramin; suramin sodium, SWOG CMFVP (cyclophosphamide, methotrexate, 5-fluorouracil, vincristine, prednisone); synercid; T-2 protocol (dactinomycin, Adriamycin, vincristine, cyclophosphamide, radiation); T-10 protocol (methotrexate, calcium leucovorin rescue, Adriamycin, cisplatin, bleomycin,; cyclophosphamide, dactinomycin); T4N5 (T4 endolase V, liposome encapsulated); Tace (chlorotrianisene); TAD (6-thioguanine, ara-C, daunomycin); talisomycin; tallimustine; TAM (tamoxifen); tamoxifen; Tarabine PFS (cytarabine); Tasmar; tauromustine; Taxol (paclitaxel); Taxotere (docetaxel); TBC-CEA; TBI (total body irradiation); TC (6-thioguanine, cytarabine); T-CAP (Baker Antifol, cyclophosphamide, Adriamycin, Platinol); T-CAP III (triazinate, cyclophosphamide, Adriamycin, Platinol); TCN-P (triciribine phosphate); TEC (thiotepa, etoposide, carboplatin); teceleukin; teleleukin; teloxantrone; temozolomide; TEMP (tamoxifen, etoposide, nitoxantrone, Platinol); teniposide (VeeM-26); terephthalamidine; teroxirone; Teslac (testolactone); TESPA (thiotepa); Testamone (testosterone); Testaqua; Testex (testosterone); testolactone; Testone (testosterone); Testred (testosterone); Testrin (testosterone); Testroject (testosterone); TFN tumor factor necrosis; Theelin Aqueous (estrone); TheraCys (BCG vaccine); Theradex (AD-32); TheraSeed; thiamiprine; thioguanine (Lanvis or 6-TG or 6-thioguanine); 6-thioguanine (6-TG or thioguanine); 6-TG (6-thioguanine); thiosulfate; thiotepa (STEPA or TESPA or TTPA); thymidine; Thymosin Alpha-I; thymidine; Thyroid Strong; tiamiprine; tiazofurin; Tiazole; Tice BGC; T-inzole (tizofurin); tirapazamine; Tiratricol; tizofurine; TLC D-99 (liposome-encapsulated doxorubicin); TMCA; T-MOP (6-thioguanine, methotrexate, Oncovin, prednisone); TMP (trimethoprim); TMQ (trimetrexate); TMTX (trimetrexate); TMX (tamoxifen); TNF (tumor necrosis factor); TNP 470; TOAP (thioguanine, Oncovin, cytosine arabinoside, prednisone); Tomosar (menogaril); Tomudex (ICI D1694), topotecan (hycamptamine); toremifene; TPCH (thioguanine, procarbazine, CCNU, hydroxyurea); TPDC-FUHU; TPDCV (thioguanine, procarbazine, DBC, CCNU, vincristine); TRA (trans-retinoic acid or tretinoin); trans-retinoic acid (TRA); TRAP (thioguanine, rubidomycin, ara-C, prednisone); trestolone; tretinoin (all trans-retinoic acid); triacana (tiratricol); triciribine phosphate; triethylene melamine; trifluoperazine; trilostane; trimetrexate; triptorelin; TSPA (thiotepa); TTPA (thiotepa); tubulozole; tumor necrosis factor (TNF); UFT (Uracil+Ftorafur); uracil mustard; uramustine; uredepa; VA (vincristine, Adriamycin); VAAP (vincristine, asparaginase, Adriamycin, prednisone); VAB 1 (vinblastine, actinomycin D, bleomycin); VAB 2 (vinblastine, actinomycin D, bleomycin, cisplatin); VAB 3 (vinblastine, actinomycin D, bleomycin, cisplatin, chlorambucil, cyclophosphamide); VAB 4 (vinblastine, actinomycin D, bleomycin, cisplatin, cyclophosphamide); VAB 5 (vinblastine, actinomycin D, bleomycin, cisplatin, cyclophosphamide); VAB 6 (cyclophosphamide, dactinomycin, vinblastine, bleomycin, cisplatin); VABCD (vinblastine, Adriamycin, bleomycin, CCNU, DTIC); VAB-V (vinblastine, actinomycin D, bleomycin, cyclophosphamide, cisplatin); VABCD (vinblastine, Adriamycin, bleomycin, CCNU, DTIC); VAC (vincristine, actinomycin D, cyclophosphamide); VAC (vincristine, Adriamycin, cyclophosphamide); VACA (vincristine, actinomycin D, cyclophosphamide, Adriamycin); VACAD (vincristine, Adriamycin, cyclophosphamide, actinomycin D, dacarbazine); VACP (VePesid, Adriamycin, cyclophosphamide, Platinol); VAD (vincristine, Adriamycin, dexamethasone); VAD/V (vincristine, Adriamycin, dexamethasone, verapamil); VAFAC (vincristine, amethopterin, 5-fluorouracil, Adriamycin cyclophosphamide); VAI (vincristine, actinomycin D, ifosfamide); Valergen; VAM (VP-26-213, Adriamycin, methotrexate); VAMP (vincristine, Adriamycin, methotrexate, prednisone); VAMP (vincristine, amethopterin, 6-mercaptopurine, prednisone); VAP (vincristine, Adriamycin, procarbazine); VAP (vincristine, asparaginase, prednisone); VAP-II (vinblastine, actinomycin D, Platinol); vapreotide; VAT (vinblastine, Adriamycin, thiotepa); VAT (vincristine, ara-A, 6-thioguanine); VATD (vincristine, ara-C, 6-thioguanine, daunorubicin); VATH (vinblastine, Adriamycin, thiotepa, Halotestin); VAV (VP-26-213, Adriamycin, vincristine); VB (vinblastine, bleomycin); VBA (vincristine, BCNU, Adriamycin); VBAP (vincristine, BCNU, Adriamycin, prednisone); VBC (VePesid, BCNU, cyclophosphamide); VBC (vinblastine, bleomycin, cisplatin); VBD (vinblastine, bleomycin, DDP); VBL (vinblastine); VBM (vincristine, bleomycin, DDP); VBMCP (vincristine, BCNU, melphalan, cyclophosphamide, prednisone); VBMF (vincristine, bleomycin, methotrexate, 5-fluorouracil); VBP (vinblastine, bleomycin, Platinol); VC (VP-16, carboplatin); VCAP (vincristine, cyclophosphamide, Adriamycin, prednisone); VCAP-I (VP-16, cyclophosphamide, Adriamycin, Platinol); VCF (vincristine, cyclophosphamide, 5-fluorouracil); VCMP (vincristine, cyclophosphamide, melphalan, prednisone); VCP (vincristine, cyclophosphamide, prednisone); VCP-I (VP-16, cyclophosphamide, Platinol); VCR (vincristine); VDP (vincristine, daunorubicin, prednisone); VDS (vindesine); VeeM-26 (teniposide); VeIP (Velban, ifosfamide, Platinol); Velban (vinblastine sulfate); Velsar (vinblastine sulfate); VEMP (vincristine, Endoxan, 6-mercaptopurine, prednisone); VePesid (etoposide or VP-16); Vercyte (pipobroman); verteprofin; Vesanoid (all trans-retinoic acid); VIC (vinblastine, ifosfamide, CCNU); VIC (VP-16, ifosfamide, carboplatin); VIE (vincristine, ifosfanide, etoposide); vinblastine; vincaleukoblastine; Vincasar; vincristine; vindesine; vinepidine; vinglycinate; vinleurosine; vinorelbine (Navelbine); vinrosidine; vinzolidine; VIP (VePesid, ifosfamide, Platinol); VIP-B (VP-16, ifosfamide, Platinol, bleomycin); VLB (vinblastine); VLP (vincristine, L-asparaginase, prednisone); VM-26 (teniposide); VM-26PP (teniposide, procarbazine, prednisone); VMAD (vincristine, methotrexate, Adriamycin, actinomycin D); VMC (VP-16, methotrexate, citrovorum factor); VMCP (vincristine, melphalan, cyclophosphamide, prednisone); VMP (VePesid, mitoxantrone, prednimustine); VOCA (VP-16, Oncovin, cyclophosphamide, Adriamycin); VOCAP (VP-16-213, Oncovin, cyclophosphamide, Adriamycin, Platinol); vorozole; VP (vincristine, prednisone); VP-16; VP-16-213; VP-16+DDP (etoposide, cisplatin); VP-16-P (VP-16, Platinol); VP+A (vincristine, prednisone, asparaginase); VPAM (verapamil); VPB (vinblastine, Platinol, bleomycin); VPBCPr (vincristine, prednisone, vinblastine, chlorambucil, procarbazine); VPCA (vincristine, prednisone, cyclophosphamide, ara-C); VPCMF (vincristine, prednisone, cyclophosphamide, methotrexate, 5-fluorouracil); VP+L-asparaginase (vincristine, prednisone, L-asparaginase); VPP (VePesid, Platinol); VPVCP (vincristine, prednisone, vinblastine, chlorambucil, procarbazine); Vumon (teniposide); Wayne State protocol (cisplatin, 5-fluorouracil); Wehgen (estrone); Wellcovorin (leucovorin); Xomazyme-791 (anti-TAP-72 immunotoxin); Xomazyme-H65 (CD5-T-lymphocyte immunotoxin); Zadaxin (thymosin alpha 1); Zanosar (streptozocin); zanoterone; ZD 0490; ZD 1694; ZDV (zidovudine); ZDX (goserelin); Zeneca 182,780; zidovudine; zinostatin; Zofran (ondansetron HCl); Zoladex (goserelin acetate), and implant; zolimomab aritox (anti-T lymphocyte monoclonal antibody); zorubicin; zorubicin HCl; Zyloprim; The present invention also contemplates high throughput screening of agents for treating psychiatric and neurological conditions and disorders. The following agents, and modifications of the following agents, including including analogs, derivatives, fragments, active moieties, and the like, may be screened using methods and systems of the present invention:; Adapin (Doxepin); Alprazolam; Amantadine; Amitriptyline; Amoxapine; Anafranil (Clomipramine); Antabuse (Disulfiram); Artane (Trihexyphenidyl); Asendin (Amoxapine); Ativan (Lorazepam); Aventyl (Nortriptyline); Benadryl (Diphenhydramine); Benztropine; Bupropion; Buspar (Buspirone); Buspirone; Calan (Verapamil); Calcium Carbimide; Carbamazepine; Carbolith (Lithium); Celexa (Citalopram); Chlordiazepoxide; Chlorpromazine; Cibalith-S (Lithium); Citalopram; Clomipramine; Clonazepam; Clozapine; Clozaril (Clozapine); Cogentin (Benztropine); Cylert (Pemoline); Dalmane (Flurazepam); Depakene (Valproate); Desipramine; Desyrel (Trazodone); Dexedrine (Dextroamphetamine); Dextroamphetamine; Diazapam; Dilantin (Phenytoin), Divalproex; Diphenhydramine; Disulfiram; Doxepin; Duralith (Lithium); Edronax (Reboxetine); Effexor (Venlafaxine); Elavil (Amitriptyline); Endep (Amitriptyline); Epitol (Carbamazepine); Epival (Divalproex); Eskalith (Lithium); Ethosuximide; Etrafon (Perphenazine); Fluanxol (Flupenthixol); Fluoxetine; Flupenthixol; Fluphenazine; Flurazepam; Fluvoxamine; Halcion (Triazolam); Haldol (Haloperidol); Haloperidol; Imipramine; Imovane (Zopiclone); Inderal (Propranolol); Isoptin (Verapamil); Janimine (Imipramine); Kionopin (Clonazepam); Lamotrigine; Lamictal (Lamotrigine); Largactil (Chlorpromazine); Libritabs (Chlordiazepoxide); Librium (Chlordiazepoxide); Lithane (Lithium); Lithium; Lithizine (Lithium); Lithobid (Lithium); Lithonate (Lithium); Lithotabs (Lithium); Lorazepam; Loxapac (Loxapine); Loxapine; Loxitane (Loxapine); Ludiomil (Maprotiline); Luvox (Fluvoxamine); Manerix (Moclobemide); Maprotiline; Mellaril (Thioridazine); Mesoridazine; Methylphenidate; Moclobemide; Modecate (Fluphenazine); Mysoline (Primidone); Nardil (Phenelzine); Navane; Nefazodone; Norpramine (Desipramine); Nortriptyline; Nozinan; Olanzapine; Orap; Oxazepam; Pamelor (Nortriptyline); Parnate (Tranylcypromine); Paroxetine; Paxil (Paroxetine); Pemoline; Permitil (Fluphenazine); Perphenazine; Pertofrane (Desipramine); Phenelzine; Piportil (Pipotiazine); Pipotiazine; Primidone; Prolixin (Fluphenazine); Propranolol; Protriptyline; Prozac (Fluoxetine); Quetiapine; Reboxetine (Edronax); Restoril (Temazepam); Rhotrimine (Trimipramine); Risperidal (Risperidone); Risperidone; Ritalin (Methylphenidate); Rivotril (Clonazepam); Sabril (Vigabatrin); Serax (Oxazepam); Serentil (Mesoridazine); Seroquel (Quetiapine); Sertraline; Serzone (Nefazodone); Sinequan (Doxepin); Stelazine (Trifluoperazine); Sulpiride; Surmontil (Trimipramine); Symmetrel (Amantadine); T-Quil (Diazapam); Tegretol (Carbamazepine); Temazepam; Temposil (Calcium Carbimide); Thioridazine; Thiothixene; Thorazine (Chlorpromazine); Tofranil (Imipramine); Trazodone; Triazolam; Trifluoperazine; Trihexyphenidyl; Trilafon (Perphenazine); Trimipramine; Triptil (Protriptyline); Valium (Diazepam); Valium Injection (Diazapam); Valproate; Valproic acid; Valrelease (Valproate); Venlafaxine; Verapamil; Vivactil (Protriptyline); Vigabatrin (Sabril); Wellbutrin (Bupropion); Xanax (Alprazolam); Zarontin (Ethosuximide); Zoloft (Sertraline); Zopiclone; Zyprexa (Olanzapine); In addition, the following agents, and modifications of the following agents, including, for example, analogs, derivatives, fragments, active moieties, and the like, may be screened using methods and systems of the present invention: Acetaminophen; Acyclovir; Albuterol (oral); Albuterol, inhaled; Allopurinol; Alprazolam; Amantadine; Amikacin; Amitriptyline; Amlodipine; Amoxicillin; Amoxicillin/clavulanate; Ampicillin; Aspirin; Atenolol; Azithromycin; Aztreonam; Beclomethasone; Benzonatate; Benztropine;

Bethanechol; Bumetanide; Captopril; Carbamazepine; Cefaclor; Cefadroxil; Cefamandole; Cefazolin; Cefixime; Cefotaxime; Cefoxitin; Ceftazidime; Ceftizoxime; Ceftriaxone; Cephalexin; Chlorpromazine; Cimetidine; Ciprofloxacin; Cisapride; Clanthromycin; Clindamycin; Clonidine; Codeine; Colchicine; Desipramine; Dexamethasone; Dextromethorphan; Diazepam; Dicloxacillin; Digoxin; Digoxin Fab; Diltiazem; Diphenhydramine; Dipyridamole; Divalproex; Doxycycline; Droperidol; Enalapril; Enoxaparin; Epinephrine; Epinephrine in; sesame oil; (Sus-Phrine); Erythromycin; Estrogen,; conjugated; Ethacrynic acid; Ethosuximide; Famciclovir; Famotidine; Felbamate; Fluconazole; Plumazenil; Fluoxetine; Folic acid; Furosemide; Gabapentin; Gentamicin; Glipizide; Glucagon; Glyburide; Griseofulvin; Haloperidol; Heparin; Hydrochlorothiazide; Hydrocortisone; Hydroxyzine; Ibuprofen; Imipramine; Indomethacin; Isosorbide dinitrate; Ketorolac; Labetalol; Lactulose; Levothyroxine; Lidocaine; Lorazepam; Lovastatin; Magnesium oxide; Magnesium sulfate; Mebendazole; Meclizine; Medroxyprogesterone; Mefenamic acid; Meperidine; Methicillin; Methylergonovine; Methylphenidate; Methylprednisolone; Metoclopramide; Metolazone (Diulo; and Zaroxolyn only); Metoprolol; Metronidazole; Midazolam; Morphine sulfate; Nafcillin; Naloxone; Naproxen; Nifedipine; Nitroglycerin; Norfloxacin; Nortriptyline; Nystatin; Ofloxacin; Omeprazole; Ondansetron; Oxybutynin; Oxycodone; Pediazole; Penicillin G; Pentamadine; Perphenazine; Phenobarbital; Phenytoin; Piperacillin; Prednisolone; Prednisone; Procainamide; Prochlorperazine; Promethazine; Propranolol; Pseudoephedrine; Pyrantel pamoate; Ranitidine; Rifampin; Rimantadine; Salsalate; Sertraline; Simvastatin; Spironolactone; Succinylcholine; Sucralfate; Sumatriptan; Terazosin; Terbutaline; Tetracycline; Thiabendazole; Thiamine; Thioridazine; Ticarcillin; Ticlopidine; Tobramycin; Trazodone; Triazolam; Trimethoprim/sulfamethoxazole; Valproic acid; Vecuronium; Venlafaxine; Verapamil; Warfarin; Zidovudine.

In one specific embodiment, a combination treatment for seizures and seizure-related disorders, such as epilepsy, may comprise an ion-dependent cotransporter antagonist, preferably a cation-chloride cotransporter antagonist, administered in combination with one or more anti-convulsants or anti-epileptic drugs using a delivery system that delivers the treatment composition(s) to the central nervous system. Often the dose of the second agent may be less than the standard dosage as a consequence of the neurophysiological activity of the ion-dependent cotransporter antagonist. Illustrative second agents for treatment in combination with the subject compositions comprising ion-dependent antagonists, include, for example, phenytoin, carbamazepine, barbiturates, phenobarbital, pentobarbital, mephobarbital, trimethadione, mephenytoin, paramethadione, phenthenylate, phenacemide, metharbital, benzchlorpropanmide, phensuximide, primidone, methsuximide, ethotoin, aminoglutethimide, diazepam, clonazepam, clorazepate, fosphenytoin, ethosuximide, valporate, felbamate, gabapentin, lamotrigine, topiramate, vigrabatrin, tiagabine, zonisanide, clobazam, thiopental, midazoplam, propofol, levetiracetam, oxcarbazepine, CCPene, GYK152466 and sumatriptan. As can be readily appreciated, the above-noted compounds are only examples of suitable treatment combinations, and other compounds or similar classes of compounds are also suitable. The activity and efficacy of such compounds, and various combinations and dosages of such compounds and combinations may be assessed using the methods and systems of the present invention.

In one exemplary embodiment, candidate agent combinations for treating epilepsy are tested using screening methods of the present invention. Agents having activity as a chloride cotransporter agonist and/or antagonist may be identified using methods and systems of the present invention. Candidate compounds may be screened for chloride cotransporter agonist and/or antagonist activity using screening methods of the present invention with various types of cells in culture such as glial cells, neuronal cells, renal cells, and the like, or in situ in animal models. Screening techniques to identify chloride cotransporter antagonist activity, for example, may involve altering the ionic balance of the extracellular space in the tissue culture sample, or in situ in an animal model, by producing a higher than "normal" anionic chloride concentration. The geometrical and/or optical properties of the cell or tissue sample subject to this altered ionic balance are determined, and candidate agents are administered. Following administration of the candidate agents, the corresponding geometrical and/or optical properties of the cell or tissue sample are monitored to determine whether the ionic imbalance remains, or whether the cells responded by altering the ionic balances in the extracellular and intracellular space. If the ionic imbalance remains, the candidate agent is likely a chloride cotransporter antagonist. By screening using various types of cells or tissues, candidate compounds having a high level of glial cell chloride cotransporter antagonist activity and having a reduced level of neuronal cell and renal cell chloride cotransporter antagonist activity may be identified. Similarly, effects on different types of cells and tissue systems may be assessed.

Additionally, the efficacy of candidate compounds for treating various conditions of the central and peripheral nervous system may be assessed by simulating or inducing a condition, such as a seizure, central nervous system edema, ethanol neurotoxicity, cortical spreading depression, or the like, in a tissue sample or in situ in an animal model, monitoring the geometrical and/or optical properties of the cell or tissue sample during stimulation of the condition, administering the candidate compound, then monitoring the geometrical and/or optical properties of the cell or tissue sample following administration of the candidate compound, and comparing the geometrical and/or optical properties of the cell or tissue sample to determine the effect of the candidate compound. Similarly, the efficacy of treatment composition(s) in an animal or human subject may be monitored in situ using the optical methods and systems of the present invention.

According to yet another embodiment, screening methods of the present invention may be accomplished by performing different steps at remote locations. Thus, in vitro and in vivo screening data may be collected at one location, such as in a testing laboratory. The data relating to optical and/or geometrical properties of cell sample populations at various test stages may be collected and transmitted to a central data processor for data processing and analysis, and screening results may subsequently be transmitted to the testing laboratory or to one or more additional sites. Network and communications technologies are readily available for transmitting the required data and implementation of remote activities, involving data processing and/or analysis, may provide expedited screening results and more economical screening.

The following Examples are provided for illustrative purposes only and are not intended to limit the invention in any way.

EXAMPLE 1

Sprague-Dawley rats (male and female; 25 to 35 days old) were prepared as described in Aghajanian, A. K. and Rasmussen, K., *Synapse* 31:331, 1989; and Buckmaster, P. S., Strowbridge, B. W., Schwartzdroin, P. A., *J. Neurophysiol.* 70:1281, 1993. In most hippocampal slice experiments, simultaneous extracellular field electrode recordings were obtained from CA1 and CA3 areas. For stimulation-evoked afterdischarge (13 slices, 8 animals), the concentration of $Mg^{2+}$ in the bathing medium was reduced to 0.9 mM. A bipolar tungsten stimulating electrode was placed on the Schaffer collaterals to evoke synaptically driven field responses in CA1; stimuli consisted to 100 to 300-µs-duration pulses at an intensity of four times population-spike threshold. After discharges were evoked by a 2-s train of such stimuli delivered at 60 Hz. Spontaneous interictal-like bursts were observed in slices treated with the following modifications or additions to the bathing medium: 10 mM $K^+$ (6 slices; 4 animals; average, 81 bursts/rnin), 200 to 300 µM 4-AP (4 slices; 2 animals; average, 33 bursts/min), 50 to 100 µg M bicuculine (4 slices; 3 animals; average, 14 bursts/min), 0 mM $Mg^{2+}$ [(1 hour of perfusion) 3 slices; 2 animals; average, 20 bursts/min; (3 hours of perfusion) 2 slices, 2 animals)], 0 mM $Ca^{2+}$/6 mM KCl and 2 mM EGTA (four slices, three animals). In all treatments, perfusion with furosemide-containing medium was begun after a consistent level of bursting had been established.

For imaging of intrinsic optical signals, the tissue was illuminated with a beam of white light (tungsten filament light and lens system; Dedotec USA, Lodi, N.J.) directed through the microscope condenser. The light was controlled and regulated (power supply: Lambda Electronics, Melville, N.Y.) to minimize fluctuations and filtered (695 nm long-pass) so that the slice was transilluminated with long wavelengths (red). Image frames were acquired with a charge-coupled device camera (Dage-MTI) at 30 Hz and were digitized at 8 bits with a spatial resolution of 512 by 480 pixels by means of an Imaging Technology Series 151 imaging system; gains and offsets of the camera-control box and the analog-to-digital board were adjusted to optimize the sensitivity of the system. Imaging hardware was controlled by a 486-PC-compatible computer running software written by D. Hochman and developed with commercially available software tools (Microsoft's C/C++ Compiler and Imaging Technology's ITEX library). To increase signal-to-noise ratio, an averaged image was composed from 16 individual image-frames, integrated over 0.5 s and averaged together. An experimental series typically involved the continuous acquisition of a series of averaged images over a several minute time period; at least 10 of these averaged images were acquired as control images before stimulation. Pseudo-colored images were calculated by subtracting the first control image from subsequently acquired images and assigned a color lookup table to the pixel values. For these images, usually a linear low-pass filter was used to remove high-frequency noise and a linear-histogram stretch was used to map the pixel values over the dynamic range of the system. All operations on these images were linear so that quantitative information was preserved.

FIGS. 2A–2C show the effect of the agent furosemide on stimulation evoked afterdischarge activity in a hippocampal tissue slice comparing the field response, measurements at an extracellular electrode, and images highlighting changes in optical properties.

Figure 2:
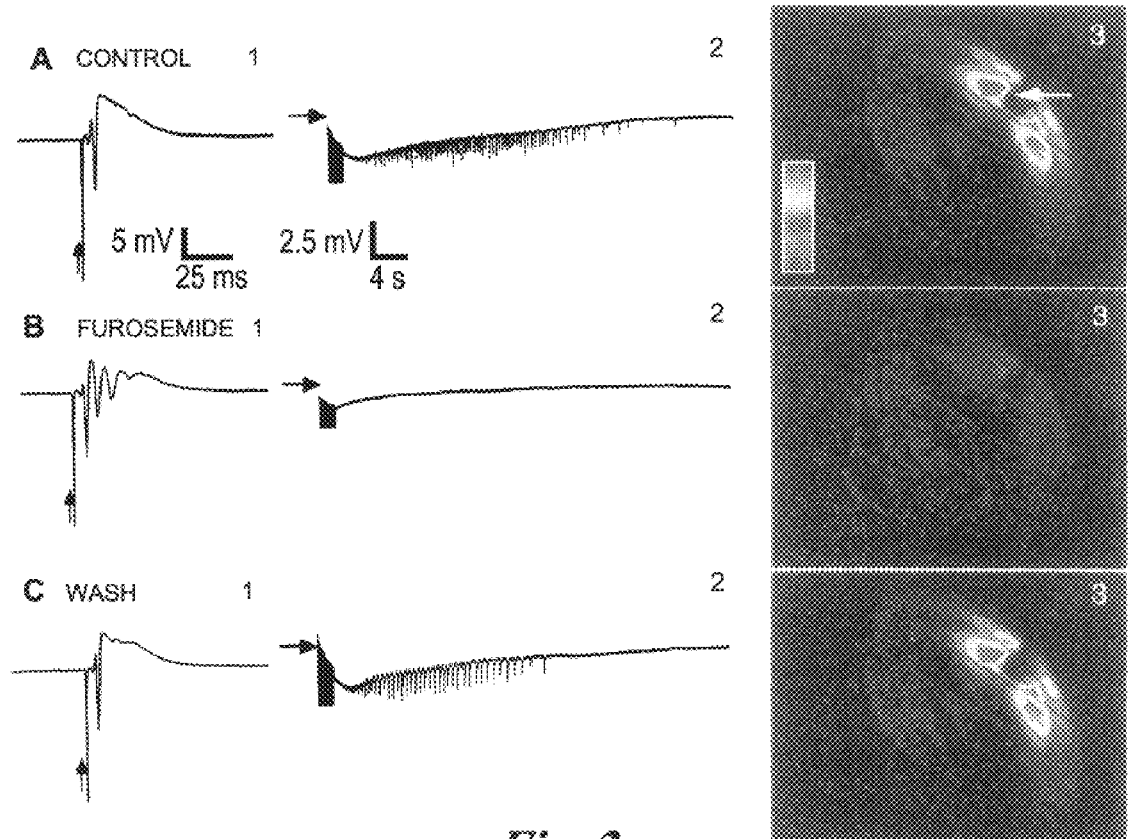

FIG. 2A1 illustrates that two seconds of electrical stimulation at 60 Hz elicited afterdischarge activity. FIG. 2A2 shows a typical afterdischarge episode recorded by the extracellular electrode, with the horizontal arrow indicating the baseline. FIG. 2A3 shows a map of the peak change in optical transmission through the tissue evoked by Schaffer collateral stimulation. The color bar indicates increasing magnitude of activity-evoked optical changes from the bottom to the top of the bar. The region of maximum optical change (red, yellow) corresponds to the apical and basal dendritic regions of CA1 on either side of the stimulating electrode. FIGS. 2B1–2BC illustrate responses to electrical stimulation following 20 minutes of perfusion with medium containing 2.5 mM furosemide. Both the electrical afterdischarge activity (shown in FIG. 2B2) and the stimulation-evoked optical changes (shown in FIG. 2BC) were blocked. However, there was a hyperexcitable field response (multiple population spikes) to the test pulse, as illustrated in FIG. 2B1. FIGS. 2C1–2C3 illustrate that restoration of the initial response pattern was seen following 45 minutes of perfusion with normal bathing medium.

Figure 3A:
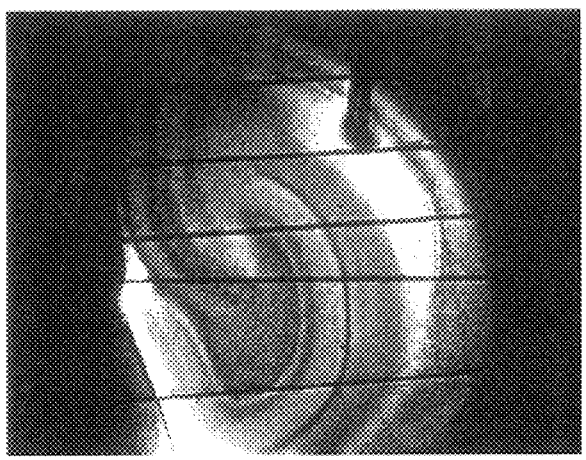
FIG. 3A illustrates an enlarged grey-scale image of an acute rat hippocampal tissue slice.
Figure 3B:
FIGS. 3B–3E illustrate enlarged, pseudo-colored images acquired as described in Example 1.
Figure 3C:
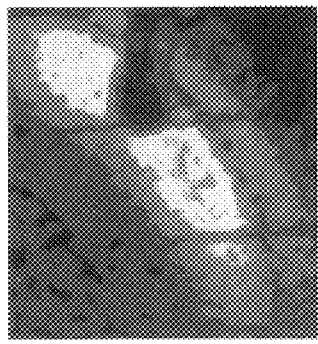
Figure 3D:
Figure 3E:

FIG. 3A illustrates an enlarged grey-scale image of an acute rat hippocampal tissue slice, observed using a CCD camera attached to a Zeiss upright microscope. FIGS. 3B–3E illustrate enlarged, pseudo-colored images acquired as described above. FIG. 3B illustrates an enlarged, pseudo-colored image acquired as described above during the peak optical change induced by electrical stimulation, with an enlarged color bar, the arrow on the color bar indicating increasing magnitude of activity-evoked optical changes. The box indicates the field of view shown magnified in FIGS. 3C, 3D and 3E. FIG. 3C illustrates the peak optical change during electrical stimulation when no epileptic activity was induced. FIG. 3D illustrates the peak optical change during electrical stimulation that resulted in epileptiform activity. A larger area of increased magnitude of changes in optical properties is observed during epileptiform activity. FIG. 3E illustrates the peak optical change during electrical stimulation following treatment with furosemide, which blocks the epileptiform activity and the intrinsic optical signal.

EXAMPLE 2

This example illustrates optical changes indicative of neuronal activity in a human subject by direct cortical electrical stimulation. Surface electrical recordings (surface EEG, ECOG) were correlated with optical changes. Intrinsic optical changes were evoked in an awake patient during stimulating-electrode "calibration." Four stimulation trials were sequentially applied to the cortical surface, each stimulation evoking an epileptiform afterdischarge episode. A stimulation trial consisted of (1) monitoring resting cortical activity by observing the output of the recording electrodes for a brief period of time; (2) applying an electric current via the stimulation-electrodes to the cortical surface at a particular current for several seconds; and (3) monitoring the output of the recording electrodes for a period of time after stimulation has ceased.

The cortex was evenly illuminated by a fiber optic emr passing through a beam splitter, controlled by a D.C. regulated power supply (Lambda, Inc.) and passed through a 695 nm longpass filter. Images were acquired with a CCD camera (COHU 6500) fitted to the operating microscope with a specially modified cineadaptor. The cortex was stabilized with a glass footplate. Images were acquired at 30 Hz and digitized at 8 bits (512×480 pixels, using an Imaging Technology Inc. Series 151 system, Woburn, Mass.). Geometric transformations were applied to images to compensate for small amounts of patient motion (Wohlberg, *Digital Imaging Warping*, IEEE Computer Society: Los Alamitos, Calif., 1988). Subtraction of images collected during the stimulated state (e.g., during cortical surface stimulation, tongue movement or naming) from those collected during a control state with subsequent division by a control image resulted in percentage difference maps. Raw data (i.e., no digital enhancement) were used for determining the average optical change in specified regions (average sized boxes was 30×30 pixels or 150–250 $\mu m^2$). For pseudocolor images, a linear low pass filter removed high frequency noise and linear histogram transformations were applied. Noise was defined as the standard deviation of fluctuations in sequentially acquired control images as 0.003–0.009.

A series of images (each image consisting of an average of 128 frames acquired at 30 Hz) were acquired during each of the four stimulation trials. A current of 6 mA was used for the first three stimulation trials, and 8 mA for the fourth. After a sequence of 3–6 averaged control images were acquired, a bipolar cortical stimulation current was applied (either 6 mA or 8 mA) until epileptiform after discharge activity was evoked (as recorded by the surface electrode). Images were continuously acquired throughout each of the four stimulation trials.

The percentage change in absorption of light for each pixel was calculated for each image acquired during the four stimulation trials. The average percentage changes over the four areas (indicated by the four square regions marked in FIG. 4A) were plotted graphically in FIGS. 4B, 4C, and 4D for comparison and analysis of the dynamic changes occurring in these four spatial areas.

Figure 4A:
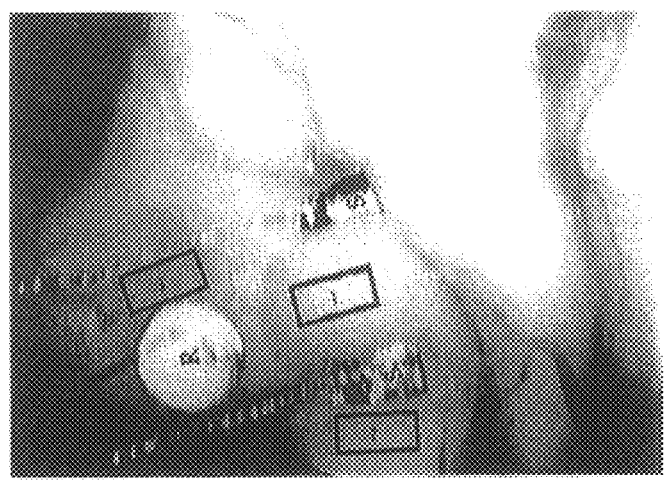
FIG. 4A illustrates a view of human cortex just anterior to face-motor cortex with one recording (R) and two stimulating (S) electrodes, and four sites (labeled 1, 2, 3, and 4), where average percent changes in corresponding optical properties were determined as described in Example 2.
Figure 4B:
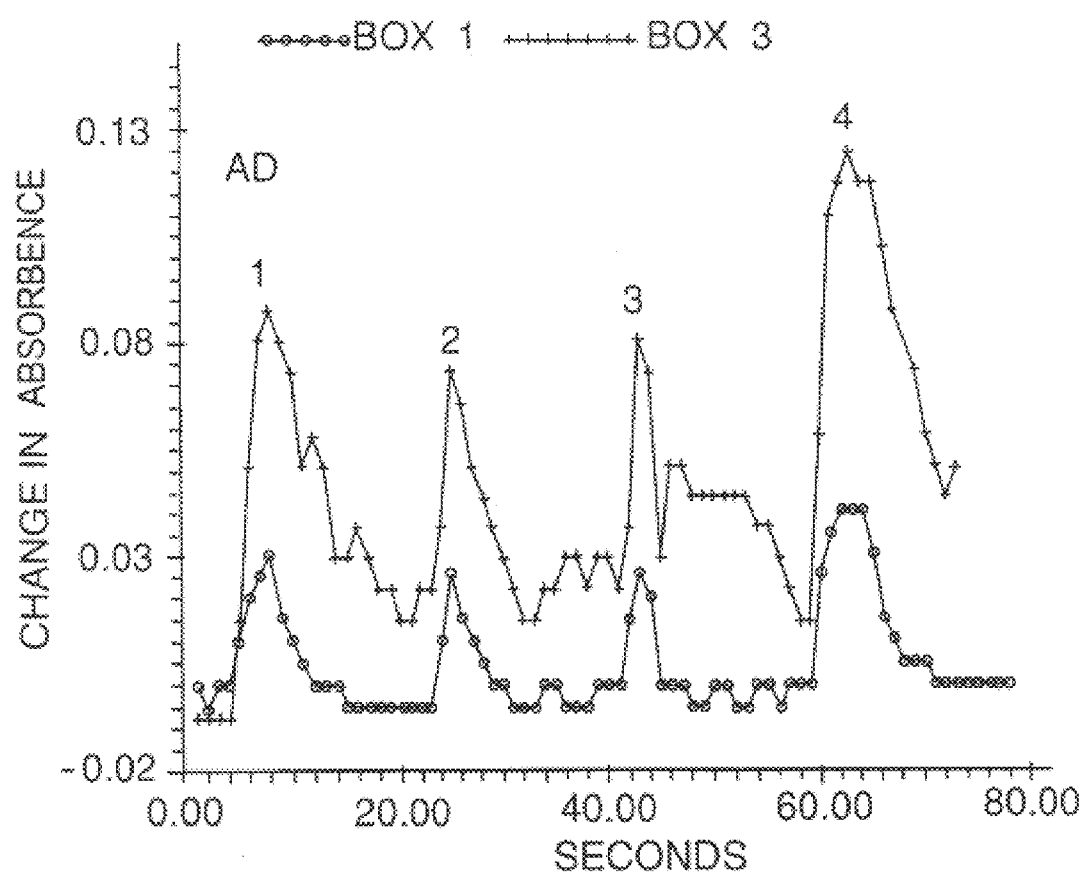
FIGS. 4B–4D illustrate plots of the percent optical changes in absorption in various spatial regions shown in FIG. 4A during electrical stimulation of the human cortex. Experiments were conducted as described in Example 2.

The optical changes between the stimulating electrodes (Site #1, FIG. 4A) and near the recording electrode (Site #3) showed a graded response to the intensity and duration of each afterdischarge episode (FIG. 4B). The spatial extent of the epileptiform activity was demonstrated by comparing a baseline image collected before stimulation to those obtained immediately after stimulation. The intensity and spread of the optical changes were much less following Stimulation #2 (shortest, least intense afterdischarge episode) than after Stimulation #4 (longest, most intense afterdischarge episode). When the optical changes were below baseline, the surface EEG recordings did not identify epileptiform activity (n=3 patients). At Site #3, the optical changes after stimulation were below baseline. However, during the fourth stimulation, the epileptiform activity spread into the area of Site #3 and the optical signal did not go below baseline until later. This negative optical signal likely represents inhibited neuronal populations (an epileptic inhibitory surround), decreased oxygen delivery, or blood volume shunted to activated regions.

FIG. 4B shows plots of the percent optical change per second in the spatial regions of Boxes 1 and 3 (as labeled in FIG. 4A). For both regions, the peak change is during the fourth stimulation trial (at 8 mA), in which the greatest amount of stimulating current had induced the most prolonged epileptiform afterdischarge activity. The changes within Box 3 were greater and more prolonged than those of Box 1. Box 3 was overlying the area of the epileptic focus.

Figure 4C:
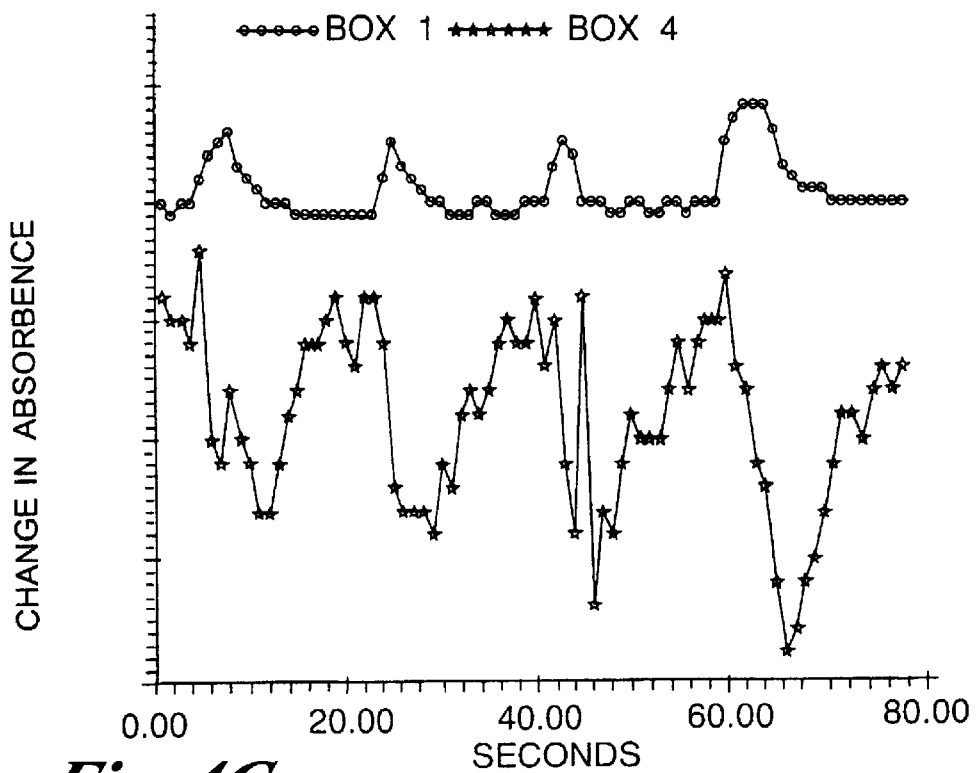

FIG. 4C shows plots of the percent optical change per second in the spatial regions of Boxes 1 and 4 (as labeled in FIG. 4A). Box 1 overlays an area of cortical tissue between the two stimulating electrodes, and Box 4 overlays a blood vessel. The optical changes within box 4 are much larger and in the opposite direction of Box 1. Also, these changes are graded with the magnitude of stimulating current and afterdischarge activity. The changes in Box 4 are most likely due to changes of the blood-flow rate within a blood vessel.

Figure 4D:
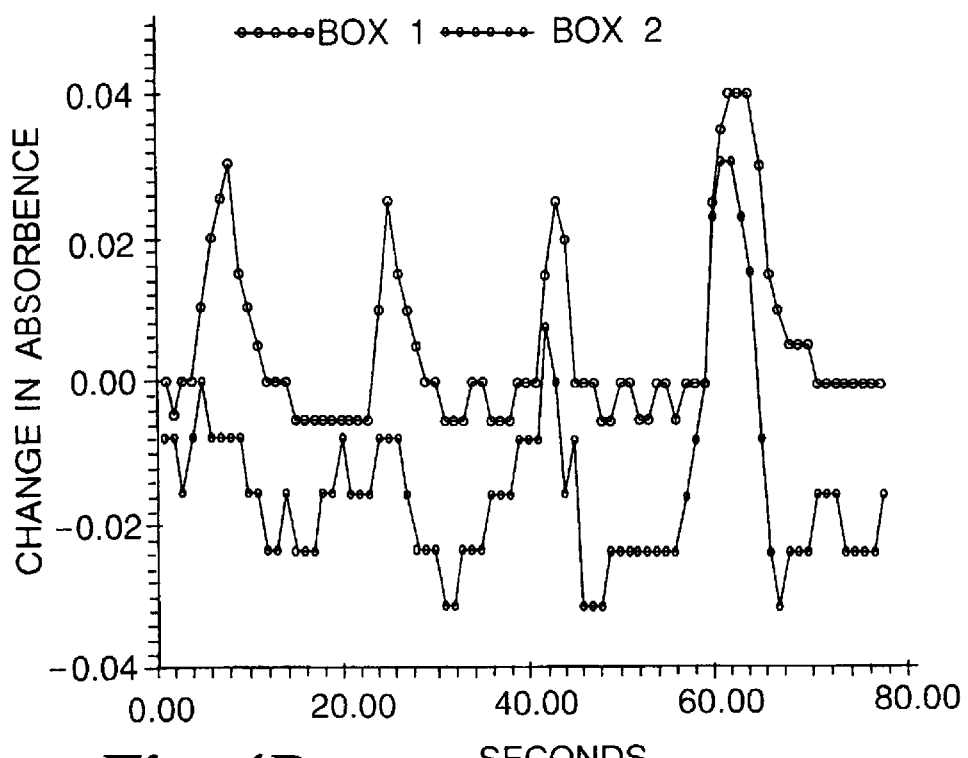
Figure 6A:
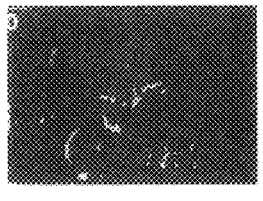
FIGS. 6A–6H illustrate percentage difference images in which the magnitude of optical change indicates the regions of greater cortical activity. Experiments were conducted as described in Example 2.
Figure 6B:
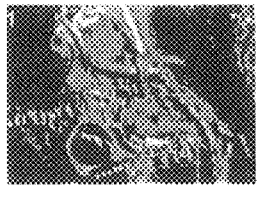
Figure 6C:
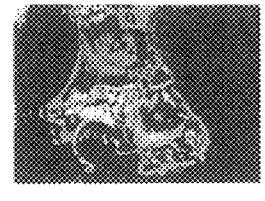
Figure 6D:
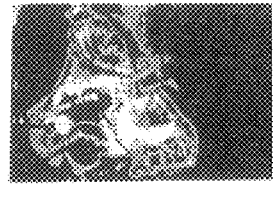
Figure 6E:
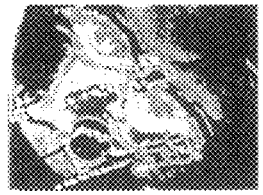
Figure 6F:
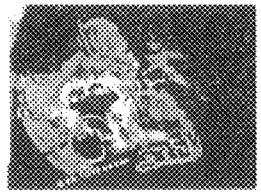
Figure 6G:
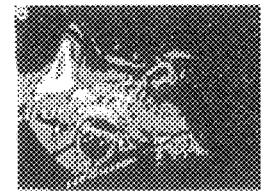
Figure 6H:
Figure 7A:
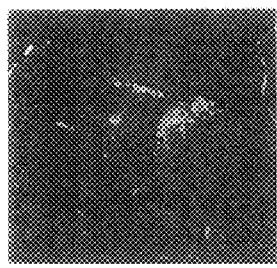
FIGS. 7A–7H illustrate percentage difference images representing a real time sequence of dynamic changes of electrical stimulation-evoked optical changes in human cortex. Experiments were conducted as described in Example 2.
Figure 7B:
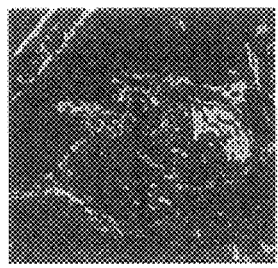
Figure 7C:
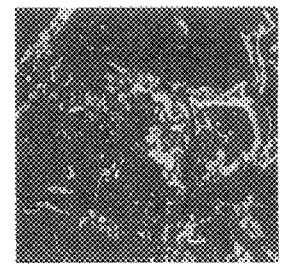
Figure 7D:
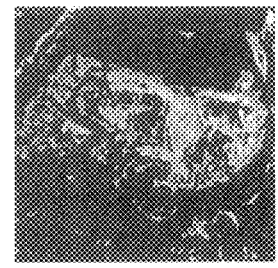
Figure 7E:
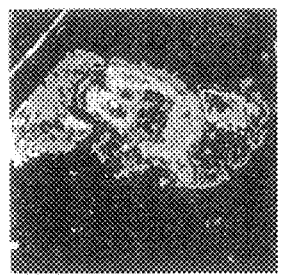
Figure 7F:
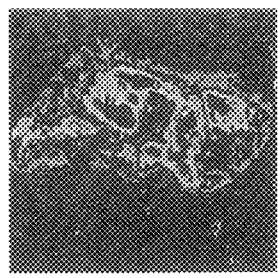
Figure 7G:
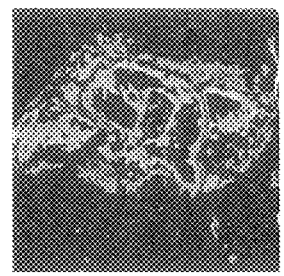
Figure 7H:
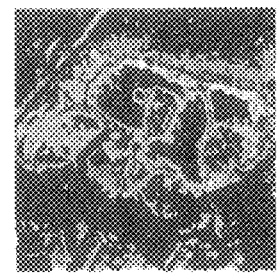

FIG. 4D shows plots of the percent optical change absorption per second in the spatial regions of boxes 1 and 2 (as labeled in FIG. 4A). Note that although these two areas are nearby each other, their optical changes are in the opposite direction during the first three stimulation trials using 6 mA current. The negative going changes within the region of Box 2 indicate that the methods and apparatus of the present invention may be used to monitor inhibition of physiological changes, as well as excitation.

FIG. 5 shows percentage difference images representative of various times during two of the stimulation trials described above. The top three images (5A2, 5B2, and 5C2) are from Stimulation Trial 2, where 6 mA cortical stimulation evoked a brief period of afterdischarge. These are compared to the bottom three images (5A4, 5B4, and 5C4), which are from Stimulation Trial 4, showing the optical changes evoked by cortical stimulation at 8 mA. FIGS. 5A2 and 5A4 compare control images during rest. FIGS. 5B2 and 5B4 compare the peak optical changes occurring during the epileptiform afterdischarge activity. FIGS. 5C2 and 5C4 compare the degree of recovery 20 seconds after the peak optical changes were observed. The magnitude of optical change is indicated by the grey-scale changes. Each image maps an area of cortex approximately 4 cm by 4 cm.

FIGS. 6A–6H show eight percentage difference images from Stimulation Trial 2, as described above. Each image is integrated over a two second interval. The focal area of greatest optical change is in the center of images 3C, 3D, and 3E, indicating the region of greatest cortical activity. This region is the epileptic focus. The magnitude of optical change is indicated by the grey-scale bar on the right side of the Figure. The arrow beside this grey-scale indicates the direction of increasing amplitude. Each image maps an area of cortex approximately 4 cm by 4 cm.

FIGS. 7A–7H illustrate a real-time sequence of dynamic changes of stimulation-evoked optical changes in human cortex. FIG. 4, panels 4A through 4H, show eight consecutive percentage difference images. Each image is an average of 8 frames (<¼ second per image). The magnitude of optical change is indicated by the grey-scale changes. Each image maps to an area of cortex that is approximately 4 cm by 4 cm. This figure demonstrates that the methods and apparatus of the present invention can be used to acquire, in real time, data reflecting dynamic changes of optical properties that reflect physiological changes.

EXAMPLE 3

Stimulation mapping of the cortical surface was performed on awake human patients under local anesthesia to identify sensory/motor cortex and Broca's areas. The illumination source and optical detection device and processing techniques used were the same as those described in Example 2. During three "tongue wiggling" trials, images were averaged (32 frames, 1 sec) and stored every 2 seconds. A tongue wiggling trial consisted of acquiring 5–6 images during rest, then acquiring images during the 40 seconds that the patient was required to wiggle his tongue against the roof of his mouth, and then to continue acquiring images during a recovery period. The same patient was then required to engage in a "language naming" trial. A language naming trial consisted of acquiring 5–8 images during rest (control images—the patient silently viewing a series of blank slides), then acquiring images during the period of time that the patient engaged in the naming paradigm (naming a series of objects presented with a slide projector every 2 seconds, selected to evoke a large response in Broca's area), and finally a series of images during the recovery period following the time when the patient ceased his naming task (again viewing blank slides while remaining silent). The results are shown in FIGS. 8 and 9.

FIGS. 8A1–8BC illustrate functional mapping of human language (Broca's area) and tongue and palate sensory areas in an awake human patient as described in Example 3. Images 8A1 and 8B1 are grey-scale images of an area of human cortex, with left being anterior, right-posterior, top-superior, and the Sylvan fissure on the bottom. The two asterisks on 8A1, 8B1, 8A2, and 8B2 serve as reference points for these images. The scale bars in the lower right comer of 8A1 and 8B1 are equal to 1 cm. In 8A1, the numbered boxes represent sites where cortical stimulation with electrical stimulating electrodes evoked palate tingling (1), tongue tingling (2), speech arrest-Broca's areas (3,4) and no response (11, 12, 17, 5, 6–7 premotor). Image 8A2 is a percentage difference control image of the cortex during rest in one of the tongue wiggling trials. The grey-scale bar on the right of 8A2 shows the relative magnitude of the grey values associated with images 8A2, 8A3, 8B2 and 8B3. Image 8A3 is a percentag difference map of the peak optical changes occurring during one of the tongue wiggling trials. Areas identified as tongue and palate sensory areas by cortical stimulation showed a large positive change. Suppression of baseline noise in surrounding areas indicated that, during the tongue wiggling trials, language-motor areas showed a negative-going optical signal. Image 8B2 is percentage difference control image of the cortex during one of the language naming trials. Image 8B3 is a percentage difference image of the peak optical change in the cortex during the language naming task. Large positive-going signals are present in Broca's area. Negative-going signals are present in tongue and palate sensory areas.

Figure 9A:
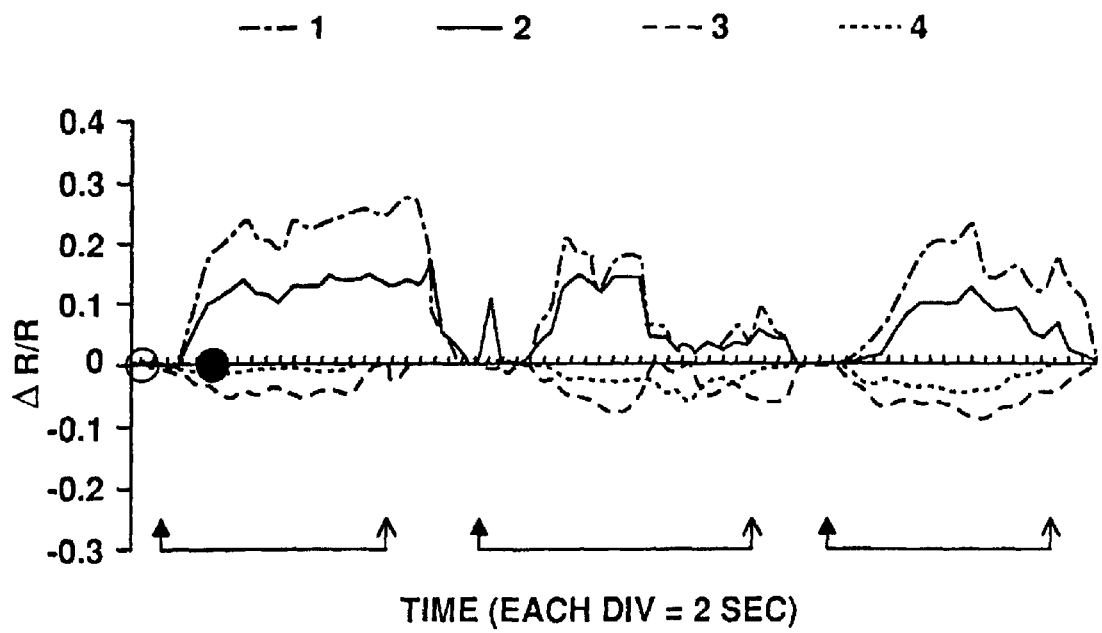
FIGS. 9A and 9B show time course and magnitude plots of dynamic optical changes in human cortex evoked in tongue and palate sensory areas and in Broca's area (language). Experiments were conducted as described in Example 3.
Figure 9B:
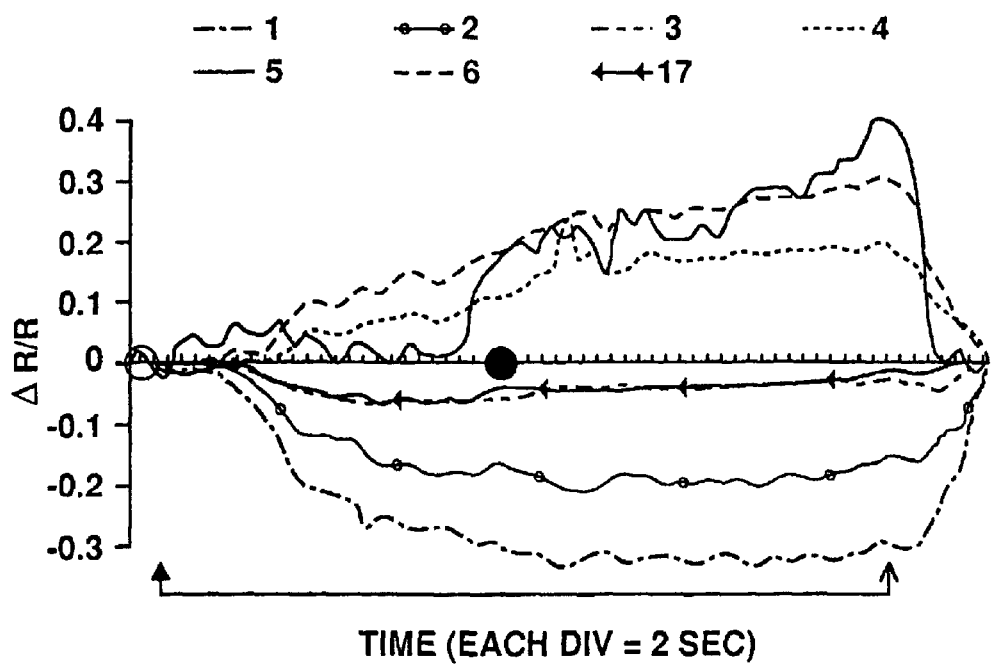

FIG. 9 shows time course and magnitude plots of dynamic optical changes in human cortex evoked in tongue and palate sensory areas and in Broca's area (language). This figure shows the plots of the percentage change in the optical absorption of the tissue within the boxed regions shown in FIG. 8, images 8A1 and 8B1, during each of the three tongue wiggling trials and one of the language naming trials (see description of FIG. 8). FIG. 9A shows the plots during the three tongue wiggling trials averaged spatially within the Boxes 1, 2, 3, and 4 as identified in FIG. 8A1. FIG. 9B shows the plots during one ofthe language naming trials averaged spatially within the Boxes 1–7 and 17.

These results agree with those data reported by Lee, et al. (*Ann. Neurol.* 20:32, 1986), who reported large electrical potentials in the sensory cortex during finger movement. The magnitude of the optical changes in the sensory cortex during tongue movement (10–30%) parallels sensory/motor cortex studies where cerebral blood flow increases 10–30% during motor tasks (Colebatch et al., *J. Neurophysiol.* 65:1392, 1991). Further, utilizing Magnetic Resonance Imaging (MRI) of blood volume changes in human visual cortex during visual stimulation, investigators have demonstrated increases of up to 30% in cerebral blood volume (Belliveau et al., *Science* 254:716, 1991).

Optical images were obtained from this same cortical region (i.e., area of interest) while the patient viewed blank slides and while naming objects on slides presented every two seconds. Percentage difference maps obtained during naming showed activation of the premotor area. The sites of speech arrest and palate tingling were identified by surface stimulation and demonstrate optical signals going in the opposite direction. The area of activation was clearly different from that evoked by tongue movement without speech production. The optical images of premotor cortex activation during naming were in similar locations to the cortical areas identified in PET single word processing studies (Peterson, et al., *Nature* 331:585, 1991; and Frith et al., *J. Neuropsychologia* 29:1137, 1991). The optical changes were greatest in the area of the cortex traditionally defined as Broca's area and not in areas where electrical stimulation caused speech arrest.

EXAMPLE 4

Areas of interest can be imaged through intact tissues, such as bone, dura, muscle, connective tissue and the like. FIGS. 10A–10D illustrate identification of a brain tumor through the intact cranium using optical imaging techniques of the present invention.

Figure 10A:
FIGS. 10A–10D illustrate the cranial surface of a rat, imaged through the intact cranium, and using a contrast enhancing agent to highlight areas of optical change. Experiments were conducted as described in Example 4.
Figure 10B:
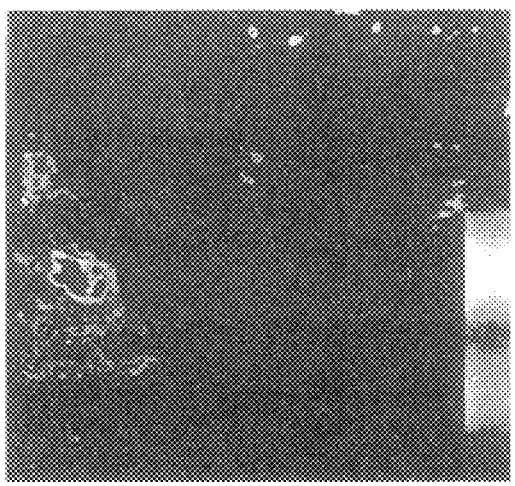
Figure 10C:
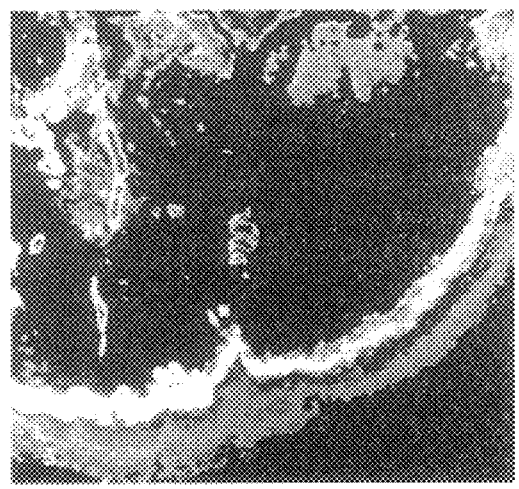
Figure 10D:

FIG. 10A is a grey-scale image of the cranial surface of a rat. The sagittal suture runs down the center of the image. Box 1 lays over the suspected region of brain tumor, and Box 2 lays over normal tissue. FIG. 10B is a difference image one second after indocyanine green dye had been intravenously injected into the animal. The region containing tumor tissue became immediately visible through the intact cranium. FIG. 10C shows that five seconds after dye injection the dye can be seen to profuse through both normal and tumor tissue. FIG. 10D shows that one minute after dye injection, the normal tissue had cleared the dye, but dye was still retained in the tumor region. The concentration of dye in the center of this difference image was dye circulating in the sagittal sinus. Dynamic changes in optical properties of cell populations and tissue may likewise be imaged in vivo through other intact tissues, such as bone, dura, muscle, connective tissue, and the like.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

I claim:

1. A method for assessing the physiological condition of a sample biological population:

maintaining at least one sample population of biological material in a viable condition;

administering a contrast agent to the sample population;

acquiring a test data set containing information relating to one or more optical properties of resolved spatial locations within the sample population following administration of the contrast agent;

comparing the test data set to a comparison data set, wherein the comparison data set contains information relating to one or more optical properties of a predetermined sample population having a predetermined physiological condition; and assessing the response of the sample population to the administration of the contrast agent based on the comparison.

2. A method of claim 1, additionally comprising acquiring a plurality of test data sets at a plurality of time points following administration of the contrast agent and wherein the comparison data set(s) contain(s) data relating to one or more optical properties of the sample biological population at different time points following administration of the contrast agent.

3. A method of claim 1, wherein the optical property is selected from the group consisting of: optical scattering; optical absorption; birefringence; fluorescence and phosphorescence.

4. A method of claim 1, wherein the physiological condition is selected from the group consisting of: viable; non-viable; necrotic; apoptotic; proliferating; malignant; intracellular and extracellular pH; intracellular and extracellular reactive oxygen species; intracellular and extracellular calcium, chloride, zinc, magnesium, sodium, and potassium levels, intracellular ATP levels, cell membrane potentials; electrical-and neuronal activity; and hemodynamic properties.

5. A method of claim 1, wherein the sample population is in a viable, healthy condition prior to administration of the contrast agent.

6. A method of claim 1, additionally comprising administering a physiological challenge prior to administering the contrast agent.

7. A method of claim 6, wherein the challenge comprises an agent selected from the group consisting of: pathogens, pollutants; radiation; chemotherapeutic agents; immumodulatory agents; biological agents; infectious agents; apoptotic agents; necrotic agents; mechanical insult; stress; aging agents; or disease agents.

8. A method of claim 1, additionally comprising admnistering a test agent prior to administering the contrast agent.

9. A method of claim 1, additionally comprising administering a physiological challenge or a test agent following the acquisition of the test data and acquiring a second test data set following administration of the physiological challenge or test agent.

10. A method of claim 9, additionally comprising administering a contrast agent following administration of the physiological challenge or test agent.

11. A method of claim 1, wherein the sample population of biological material is genetically modified.

12. A method of claim 1, wherein the sample population of biological material comprises pathological cells.

13. A method of claim 1, additionally comprising simulating a disease state in the sample population prior to administration of the contrast agent.

14. A method for screening a candidate compound for activity as a diagnostic or therapeutic agent, comprising:

maintaining at least one sample population of biological material;

introducing a candidate compound and a contrast agent to the sample population;

acquiring and recording at least one test data set corresponding to one or more optical properties of the sample population following introduction of the candidate compound;

comparing the test data set to a comparison data set, wherein the comparison data set corresponds to one or more optical properties of a predetermined sample population having a predetermined physiological state; and assessing the activity of the candidate compound as a diagnostic or therapeutic agent based on the comparison between the test data set and the comparison data set.

15. The method of claim 14, wherein the optical property is selected from the group consisting of: optical scattering; optical absorption; birefringence; fluorescence and phosphorescence.

16. The method of claim 14, wherein the sample population of biological material comprises pathological cells.

17. The method of claim 14, wherein the sample population of biological material comprises malignant cells.

18. The method of claim 14, wherein the sample population of biological material comprises dysfunctional cells.

19. The method of claim 14, wherein the candidate compound is suspected of having activity as a chloride cotransporter agonist or antagonist.

* * * * *